(12) United States Patent
Oliveira et al.

(10) Patent No.: US 11,013,667 B2
(45) Date of Patent: May 25, 2021

(54) NASOGASTRIC TUBE SECUREMENT SYSTEMS AND METHODS OF USING SAME

(71) Applicant: 3M INNOVATIVE PROPERTIES COMPANY, St. Paul, MN (US)

(72) Inventors: Jener de Oliveira, Sumare-SP (BR); Elaine C. Ramires, Campinas-SP (BR); Adriana S. P. Lovon, São Paulo (BR); Steven B. Heinecke, New Richmond, WI (US); Simon S. Fung, Woodbury, MN (US); Felipe S. R. Bizarria, São Paulo (BR)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 453 days.

(21) Appl. No.: 15/751,701

(22) PCT Filed: Aug. 18, 2016

(86) PCT No.: PCT/US2016/047491
§ 371 (c)(1),
(2) Date: Feb. 9, 2018

(87) PCT Pub. No.: WO2017/034909
PCT Pub. Date: Mar. 2, 2017

(65) Prior Publication Data
US 2018/0228699 A1    Aug. 16, 2018

Related U.S. Application Data

(60) Provisional application No. 62/208,058, filed on Aug. 21, 2015.

(51) Int. Cl.
*A61J 15/00* (2006.01)
*A61M 25/02* (2006.01)

(52) U.S. Cl.
CPC ....... *A61J 15/0061* (2013.01); *A61J 15/0003* (2013.01); *A61M 25/02* (2013.01);
(Continued)

(58) Field of Classification Search
CPC .. A61J 15/0061; A61J 15/0003; A61M 25/02; A61M 2025/0253; A61M 2025/026
(Continued)

(56) References Cited

U.S. PATENT DOCUMENTS

RE24,906 E     12/1960  Ulrich
3,389,827 A     6/1968  Abere
(Continued)

FOREIGN PATENT DOCUMENTS

CN     102940581     2/2013
CN     203154338     8/2013
(Continued)

OTHER PUBLICATIONS

International Search Report for PCT International Application No. PCT/US2018/020145, dated May 24, 2018.
(Continued)

*Primary Examiner* — Brandy S Lee
*Assistant Examiner* — Nidah M Hussain
(74) *Attorney, Agent, or Firm* — 3M Innovative Properties Company; Trisha D. Adamson

(57) ABSTRACT

A nasogastric tube securement system. The system can include a base layer and a coupling layer. The base layer can be configured to be adhered to a nose, the base layer having a first major surface comprising a skin-contact adhesive and a second major surface opposite the first major surface. The coupling layer can include a first end comprising coupling means configured to be repositionably coupled to the second major surface of the base layer, and a leg. The leg can be connected to and extending from the first end, can be elongated along a longitudinal direction, and can be configured to secure a nasogastric tube.

21 Claims, 9 Drawing Sheets

(52) U.S. Cl.
CPC ............... *A61M 2025/026* (2013.01); *A61M 2025/0226* (2013.01); *A61M 2025/0253* (2013.01)

(58) Field of Classification Search
USPC ....................................................... 604/516
See application file for complete search history.

(56) References Cited

U.S. PATENT DOCUMENTS

| | | | |
|---|---|---|---|
| 3,645,835 | A | 2/1972 | Hodgson |
| 4,112,213 | A | 9/1978 | Waldman |
| 4,310,509 | A | 1/1982 | Berglund |
| 4,323,557 | A | 4/1982 | Rosso |
| 4,534,762 | A * | 8/1985 | Heyer ............... A61M 25/02 128/DIG. 26 |
| 4,595,001 | A | 6/1986 | Potter |
| 4,737,410 | A | 4/1988 | Kantner |
| 4,986,815 | A | 1/1991 | Schneider |
| 5,088,483 | A | 2/1992 | Heinecke |
| 5,156,641 | A * | 10/1992 | White ............... A61M 25/02 128/207.18 |
| 5,160,315 | A | 11/1992 | Heinecke |
| 5,172,688 | A | 12/1992 | Dillon |
| 5,531,855 | A | 7/1996 | Heinecke |
| 5,735,272 | A | 4/1998 | Dillon |
| 6,264,976 | B1 | 7/2001 | Heinecke |
| 7,947,366 | B2 | 5/2011 | Ishiwatari |
| 2001/0029954 | A1 | 10/2001 | Palmer |
| 2002/0143296 | A1* | 10/2002 | Russo ............... A61M 25/02 604/180 |
| 2005/0171482 | A1* | 8/2005 | Russo ............... A61M 25/02 604/180 |
| 2009/0137961 | A1* | 5/2009 | Bracken ............ A61M 25/02 604/177 |
| 2009/0292256 | A1 | 11/2009 | Cubberly |
| 2010/0121281 | A1 | 5/2010 | Luhrs |
| 2010/0199997 | A1* | 8/2010 | McInnes .......... A61M 25/02 128/207.14 |
| 2011/0253146 | A1 | 10/2011 | Jundt |
| 2012/0029435 | A1 | 2/2012 | Gutierrez Del Rio |
| 2012/0138060 | A1 | 6/2012 | Barlow |
| 2015/0086741 | A1* | 3/2015 | Karim ............... C09J 5/00 428/41.8 |

FOREIGN PATENT DOCUMENTS

| | | |
|---|---|---|
| CN | 203227187 | 10/2013 |
| EP | 0845278 | 6/1998 |
| EP | 2532384 | 12/2012 |
| JP | S92346 | 1/1984 |
| QA | WO 1989-001349 | 2/1989 |
| WO | WO 1986-006641 | 11/1986 |
| WO | WO 1994-028962 | 12/1994 |
| WO | WO 1998-032481 | 7/1998 |
| WO | WO 2005-025664 | 3/2005 |
| WO | WO 2010-056541 | 5/2010 |
| WO | WO 2010-056543 | 5/2010 |
| WO | WO 2010-056544 | 5/2010 |
| WO | WO 2012-009126 | 1/2012 |
| WO | WO 2013-096103 | 6/2013 |
| WO | WO 2013-162680 | 10/2013 |
| WO | WO 2014-092703 | 6/2014 |
| WO | WO 2017-034907 | 3/2017 |
| WO | WO 2017-034911 | 3/2017 |
| WO | WO 2017-034912 | 3/2017 |
| WO | WO 2017-034913 | 3/2017 |

OTHER PUBLICATIONS

International Search Report for PCT International Application No. PCT/US2016/047489, dated Dec. 12, 2016.
International Search Report for PCT International Application No. PCT/US2016/047494, dated Dec. 12, 2016.
International Search Report for PCT International Application No. PCT/US2016/047495, dated Dec. 12, 2016.
International Search Report for PCT International Application No. PCT/US2016/047500, dated Dec. 12, 2016.
International Search Report for PCT International Application No. PCT/IB2018/050284, dated Jun. 25, 2018.
International Search Report for PCT International Application No. PCT/US2016/047491 dated Dec. 12, 2016, 7 pages.

* cited by examiner

NASOGASTRIC TUBE SECUREMENT SYSTEMS AND METHODS OF USING SAME

CROSS REFERENCE TO RELATED APPLICATIONS

This application is a national stage filing under 35 U.S.C. 371 of PCT/US2016/047491, filed Aug. 18, 2016, which claims the benefit of U.S. Provisional Application No. 62/208,058, filed Aug. 21, 2015, the disclosure of which is incorporated by reference in its entirety herein.

FIELD

The present disclosure generally relates to nasogastric tube securement systems, and methods of using same, and particularly to systems configured to be secured to skin.

BACKGROUND

During patient treatment (e.g., at hospitals, and particularly, in Intensive Care Units (ICUs)), the insertion of tubes can be required for different purposes, such as feeding, air supply, and/or liquid removal. The tubes inserted through the nose are referred to as nasogastric (NG) tubes and can be used for various applications, including feeding, drug administration and/or stomach drainage. Such nasogastric tubes generally need to be attached to the patient's skin in order to maintain the correct position internally, such as inside the stomach.

Some existing devices for NG tube securement do not allow a medical practitioner (e.g., a nurse) to intervene or evaluate the position or level of securement without removing an adhesive tape from skin, which can cause damage to the patient's skin (such as skin tears, redness, and/or damages due to constant changing of adhesives). Other existing devices are large and bulky (e.g., configured to be attached around the patient's head), thereby being cumbersome to use, reducing patient comfort, and/or causing pressure ulcers.

SUMMARY

As a result, there is a need for robust, reliable, manipulatable, repositionable nasogastric tube securement systems, which provide for a standardization of procedures. The nasogastric tube securement systems of the present disclosure can increase the safety of NG tube securement and patient's comfort, while minimizing skin damage. Systems of the present disclosure generally allow for repositioning of the NG tube and/or the system (or a portion thereof) relative to a patient (e.g., the patient's skin, the nose, and/or an internal structure) when needed. In general, systems of the present disclosure include a base layer for securing the system to a patient's nose, and a coupling layer configured to be repositionably coupled to the base layer, while also being configured to secure the NG tube. The coupling layer can be repositioned without removing the base layer from the skin or even changing the base layer (e.g., comprising an adhesive tape) on the skin. In view of that, the comfort is enhanced and any potential risk for skin damage can be minimized.

The nasogastric tube securement systems of the present disclosure can also reduce pressure ulcers in the nostril caused by the NG tubes, which can be a frequent problem on patients using NG tubes. The majority of tubes are secured by tapes or adhesive devices that are usually changed after 24 hours which may increase the potential risk of pressure ulcers developing in the nostril. However, by using the nasogastric tube securement systems of the present disclosure, the medical practitioner can evaluate a potential pressure point inside the nostril and take action to avoid the ulcers by changing the securement device position without causing an adhesion lesion or reducing the securement of the NG tube.

Some aspects of the present disclosure provide a nasogastric tube securement system. The system can include a base layer and a coupling layer. The base layer can be configured to be adhered to a nose, the base layer having a first major surface comprising a skin-contact adhesive and a second major surface opposite the first major surface. The coupling layer can include a first end comprising coupling means configured to be repositionably coupled to the second major surface of the base layer, and a leg. The leg can be connected to and extending from the first end, can be elongated along a longitudinal direction, and can be configured to secure a nasogastric tube. The leg can connect to the first end at a position that is located toward a lateral side of the first end, relative to a lateral center of the first end, and the first end can be wider than the leg in a lateral direction that is oriented substantially perpendicularly with respect to the longitudinal direction.

Other features and aspects of the present disclosure will become apparent by consideration of the detailed description and accompanying drawings.

DETAILED DESCRIPTION

Figure 1:
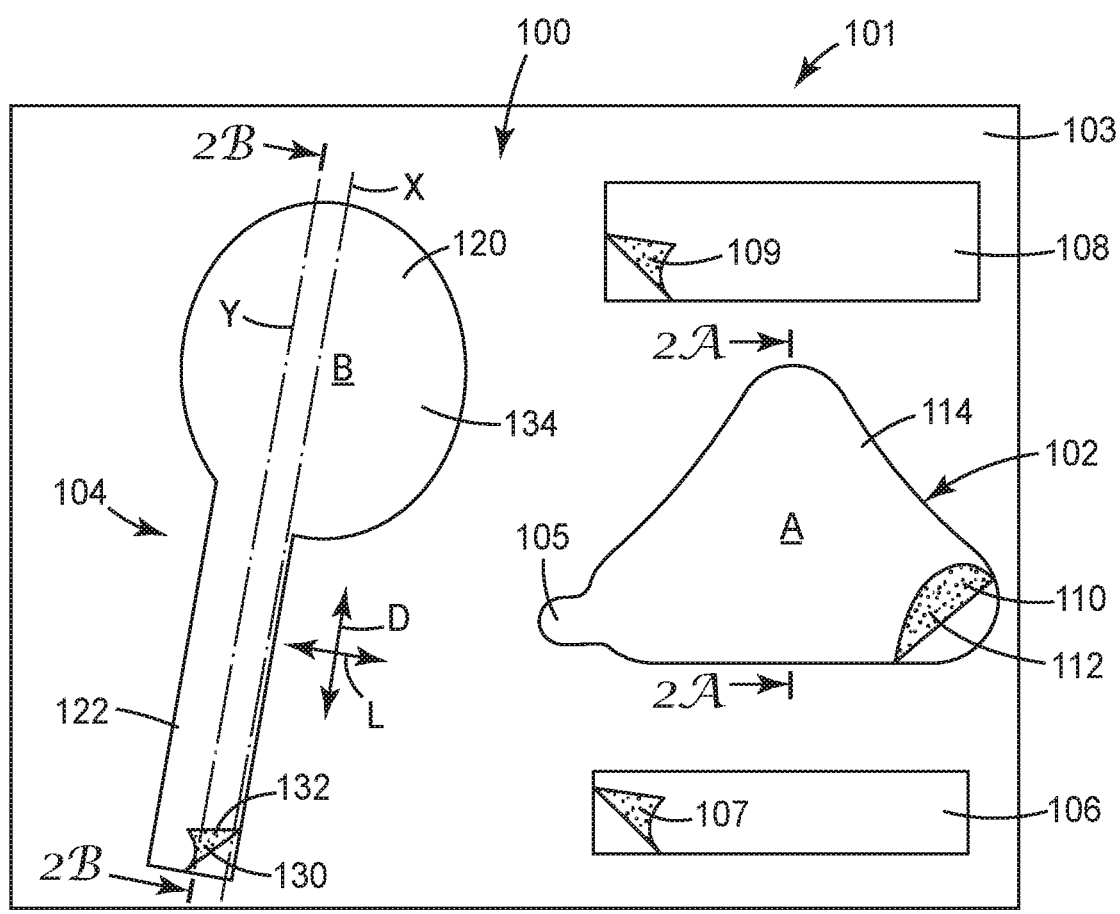
FIG. 1 is a plan view of a nasogastric tube securement system according to one embodiment of the present disclosure, the system shown in the form of a kit, the system comprising a base layer and a coupling layer.

The present disclosure generally relates to nasogastric tube securement systems and methods of using same. Particularly, nasogastric tube securement systems of the present disclosure include at least two parts or components: (i) a base layer that can be coupled (i.e., adhered) to skin, and (ii) a coupling layer having a portion configured to secure the nasogastric tube and a portion configured to be repositionably coupled to the base layer to allow the nasogastric tube to be repositioned as desired without disrupting the base layer adhesion to skin, or requiring any portion of the base layer to be removed. The base layer can remain in position on the skin until it becomes necessary to change it or until the nasogastric tube is removed from the patient.

The systems of the present disclosure can be provided together as a kit, e.g., on one release liner, which can enhance manufacturability, packaging, ease-of-use and standardization of application procedures or techniques.

As a result, the systems of the present disclosure provide a repositionable coupling layer that can be repositioned as desired on a base layer that remains stably adhered to the skin until the entire system is to be changed or removed. The repositionable coupling layer secures the nasogastric tube on the patient's nose in order to keep it well placed. This allows site evaluation and helps reduce skin damage, as well as nostril pressure ulcers.

In some embodiments, the base layer can include a release agent (e.g., a release coating) on its back side to which an adhesive on the coupling layer can be adhered to ensure that the coupling layer (or at least a portion thereof) can be repositionable on the base layer. Alternatively or additionally, in some embodiments, the base layer can include a first mating surface of a mechanical fastener (e.g., hooks) on its back side to which a second mating surface of the mechanical fastener on the coupling layer (e.g., loops) can be repositionably engaged. This will be described in greater detail below with reference to FIGS. 3A and 3B.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "connected" and "coupled," and variations thereof, are used broadly and encompass both direct and indirect connections and couplings.

The terms "layer," "sheet," and "dressing," or variations thereof, are used to describe an article having a thickness that is small relative to its length and width.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The term "repositionable" refers to the ability of an article or surface to be, at least initially, repeatedly coupled to (e.g., adhered to) and removed from a surface or substrate without substantial loss of coupling capability (e.g., adhesion) and without damage to either surface (e.g., article or underlying substrate) being coupled together. For example, a coupling layer of the present disclosure can be repositionable on a base layer of the present disclosure if the base layer and the coupling layer can be removed, or decoupled, from one another without causing damage to the base layer or the coupling layer. By way of example, some pressure-sensitive adhesives and mechanical fasteners are repositionable.

The phrase "mechanical fastener" or "touch fastener" generally refers to a fastener that includes two mating, or engagement, surfaces configured to be applied to one another, each mating surface having a plurality of engagement structures or features, such that engagement structures on one mating surface are configured to engage with the engagement structures on the opposing mating surface. In some embodiments, the mechanical fastener can include two flexible mating strips or layers. In some embodiments, the mechanical fastener can include a first mating surface comprising tiny, stiff protrusions shaped like hooks that are configured to engage a second mating surface comprising pliable loops (i.e., a "hook and loop fastener," or "hook and pile fastener"). In some embodiments, the mechanical fastener can include inter-engaging hooks (e.g., self-engaging hooks) on both mating surfaces (i.e., a "hook and hook fastener" or a "self-engaging hook fastener").

"Peel force" refers to the force needed to "peel" one surface from another surface at an angle with respect to the plane between the surfaces. Adhesive peel force can be measured using the ASTM method referenced in the "Adhesives" section below. Peel force between mating surfaces of a mechanical fastener can be measured using ASTM D5170-98 (2015)—Standard Test Method for Peel Strength ("T" Method) of Hook and Loop Touch Fasteners.

"Shear strength" (or "shear force") refers to the resistance to forces that cause, or tend to cause, two contiguous parts of a body to slide relatively to each other in a direction parallel to their plane of contact. That is, shear strength is the amount of force required to move one surface relative to another surface when the two surfaces are pulled in opposite directions parallel to their plane of contact. Adhesive shear force can be measured using the ASTM method referenced in the "Adhesives" section below. Shear force between mating surfaces of a mechanical fastener can be measured using ASTM D5169-98 (2015)—Standard Test Method for Shear Strength (Dynamic Method) of Hook and Loop Touch Fasteners.

FIG. 1 illustrates a nasogastric tube securement system 100 according to one embodiment of the present disclosure. By way of example only, the system 100 is shown as a kit 101 comprising four elements of the system 100 all provided on one release liner 103. Additional details regarding release liners of the present disclosure are described in greater detail below under the section entitle, "Release Liners." As shown in FIG. 1, the nasogastric tube securement system can include a base layer, sheet or dressing 102, a coupling layer, sheet or dressing 104, and one or more additional auxiliary layers, sheets or tapes. The base layer 102 and the coupling layer 104 can be flexible sheets.

Specifically, by way of example only, the system 100 is shown as including a first tape strip 106 and a second tape strip 108. The first tape strip 106 can include securing means, e.g., a securing adhesive 107, configured to adhere to the nasogastric tube (e.g., an outer surface thereof) and configured to be wrapped about at least a portion of a circumference of the nasogastric tube to mark a desired depth of insertion into a subject's nostril.

The second tape strip 108 can include a skin-contact adhesive 109 and can be configured to be adhered to another portion of the subject's skin (e.g., on the face) to hold a portion of the length of the nasogastric tube out of the way to inhibit accidental tensions in the nasogastric tube or accidental removal of the nasogastric tube from the nostril or nasal cavity.

The first tape strip 106 and the second tape strip 108 are shown as being elongated and rectangular by way of example; however, it should be understood that the first tape strip 106 and the second tape strip 108 can have any shape suitable for marking the nasogastric tube and for adhering a portion of the tube to the subject's skin, respectively.

With continued reference to FIG. 1, the base layer 102 can be configured (e.g., dimensioned, shaped, formed of appropriate materials, etc.) to be adhered to the skin on the top of a nose (e.g., a human nose). The base layer 102 can include a first (e.g., bottom) major surface 110 comprising a skin-contact adhesive 112 and a second (e.g., top) major surface 114 opposite the first major surface.

Additional details regarding securing adhesives and skin-contact adhesives of the present disclosure are described in greater detail below under the section entitled, "Adhesives."

The base layer 102 can be shaped to be conducive to covering a nose, and particularly, a human nose. By way of example only, the base layer 102 of FIG. 1 has a generally triangular shape comprising a center portion that can overlap and adhere to the bridge of a nose, and two side flank portions extending out from the center portion configured to overlap and adhere to the sides of a nose, providing a secure and reliable base for the system 100. Other shapes are possible to achieve a stable and secure base, as described below with respect to FIGS. 5A and 5B. In addition, the base layer 102 may be provided in various sizes to accommodate different populations, e.g., smaller sizes for children.

The coupling layer 104 can include a first bulbous end (or "first end" or "nose securing portion" or "base layer coupling portion") 120; and a leg (or "nasogastric tube securing portion") 122. In some embodiments, the coupling layer 104 consists essentially of the first end 120 and the leg 122. In some embodiments, the first end 120 can be referred to as "bulbous" because of its protruding and expanded areas or shapes, relative to the narrower leg 122.

The first end 120 can include coupling means configured to be repositionably coupled to the second major surface 114 of the base layer 102. The leg 122 can be configured to secure a nasogastric tube, i.e., can include securing means for reliably coupling the nasogastric tube. In some embodiments, it can be desirable for the leg 122 to not only securely hold the nasogastric tube for a desired duration of time but to also allow relatively easy removal of the nasogastric tube. As shown, the leg 122 connects to a lower end or portion of the first end 120 and is elongated along or parallel to a longitudinal direction D extending downwardly from the first end 120.

Furthermore, by way of example only, in some embodiments, the base layer 102 and/or the coupling layer 104 (e.g., the first end 120) can include one or more tabs 105, which can facilitate removal of the base layer 102 and/or the coupling layer 104 from the release liner 103. In addition, or alternatively, such tabs 105 can enhance removal of the base layer 102 from skin after use, and/or can enhance removal of the coupling layer 104 from the base layer 102 during use (e.g., for repositioning as necessary) or after use. To facilitate easy grasping of tabs 105, an additional section of release liner may be provided under only the portion 105.

In the embodiment illustrated in FIG. 1, the first end 120 is wider than the leg 122 in a lateral, or transverse, direction L that is oriented substantially perpendicularly with respect to the longitudinal direction D. Said another way, in some embodiments, the first end 120 has a width (i.e., an ultimate lateral dimension) in the lateral direction L that is greater than that of the leg 122. In some embodiments, as shown in FIG. 1, the first end 120 can each be at least two times wider than the leg 122. The wider first end 120 can ensure a sufficient coupling area and shear strength between the coupling layer 104 and the base layer 102, without requiring that the entire coupling layer 104 have this width, which could result in an overall large, cumbersome and bulky structure. As a result, the first end 120 is dimensioned for coupling to the base layer 102, while the leg 122 is dimensioned for effectively wrapping (or folding) about a circumference of a nasogastric tube to enhance the security of the nasogastric tube. That is, the relative sizing between the first end 120 and the leg 122 can ensure that the first end 120 can be sized appropriately for coupling to the nose (i.e., sized to be coupled over the nose via the base layer 102) and can ensure that the leg 122 can be sufficiently narrow without adding bulk, complexity or reducing patient comfort. In addition, the relative sizing can ensure that the leg 122 is sufficiently long (i.e., in the longitudinal direction D) to avoid pressure on the nostril.

Said another way, in some embodiments, the first end 120 can have a central longitudinal axis X, and the leg 122 can connect to the first end 120 at a position that is located laterally with respect to the central longitudinal axis X of the first end 120 (i.e., connects to the first end 120 at a location that is not a lateral center of the first end 120). In some embodiments, the first end 120 can be laterally symmetrical about the central longitudinal axis X. However, due to the laterally offset leg 122, the coupling layer 104 as a whole is not laterally symmetrical. Rather, the coupling layer 104 is asymmetrical.

Furthermore, the leg 122 can be oriented substantially parallel with respect to the central longitudinal axis X of the first end 120, as shown in FIG. 1. In addition, the leg 122 can have a central longitudinal axis Y that is substantially parallel to and spaced a distance from the central longitudinal axis X of the first end 120. In some embodiments, the central longitudinal axis X of the first end 120 can be oriented substantially along a bridge of a hose when the coupling layer 104 is coupled to (i.e., in place on) the nose.

Figure 4A:
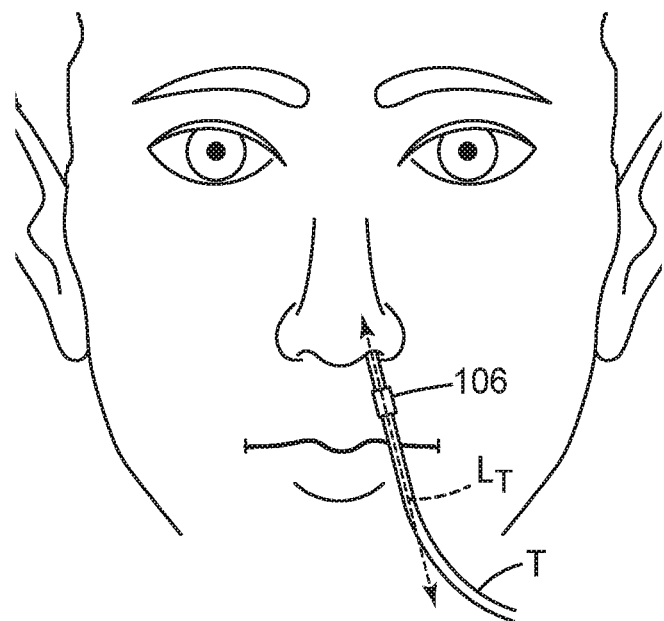
FIGS. 4A-4J illustrate a method of using the nasogastric tube securement system of FIG. 1.
Figure 4B:
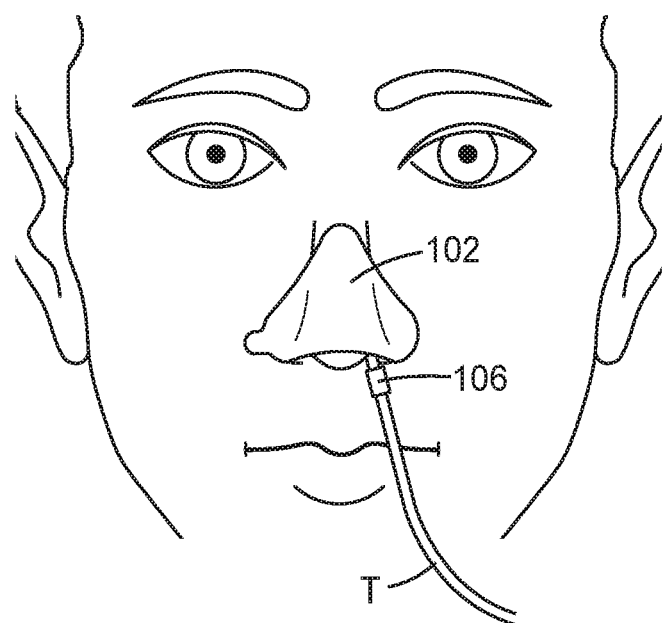
Figure 4C:
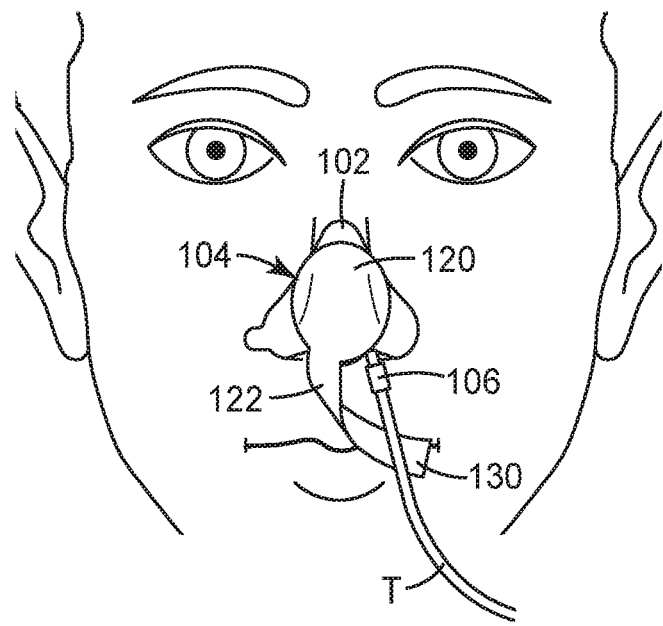

In some embodiments, as shown in FIG. 4C, which is described in greater detail below, the width of the first end 120 of the coupling layer 104 and/or the width of the base layer 102 can be oriented, in use, substantially laterally with respect to a bridge of a nose when the system 100 is coupled to the nose.

In some embodiments, the leg 122 can be longer in the longitudinal direction D than the first end 120 to ensure that the leg 122 has sufficient length to secure the nasogastric tube at a longitudinal position that will not directly impinge on the nose, nostril, or otherwise, pull or cause tension on the first end 120 of the coupling layer 104, the base layer 102, the nose, or the nostril.

In some embodiments, the coupling layer 104 is generally "p" shaped, or generally has "p" configuration, i.e., generally takes the shape of a capital or lowercase English letter "p." For example, in such embodiments, the leg 122 can connect to the first end 120 at a location that is laterally spaced from a lateral center of the first end 120. Specifically, in FIG. 1, the leg 122 connects to the first end 120 to the left of a lateral center (or a central longitudinal axis) of the first end 120.

In some embodiments, the coupling layer 104 is generally "q" shaped, or generally has a "q" configuration, i.e., generally takes the shape of a lowercase English letter "q." That is, in some embodiments, the leg 122 connects to the first end 120 to the right of a lateral center (or a central longitudinal axis) of the first end 120 (see FIG. 6B, described below).

Figure 6A:
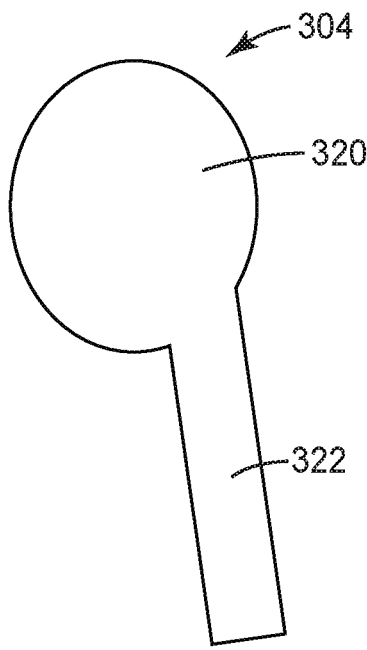
FIGS. 6A-6C each illustrate a coupling layer according to another embodiment of the present disclosure.

In some embodiments, as shown in FIG. 1, the first end 120 of the coupling layer 104 can extend laterally outwardly with respect to the leg 122, such that the leg 122 is located within the width of the first end 120. However, this need not be the case, as shown in FIG. 6A, described below.

Figure 7A:
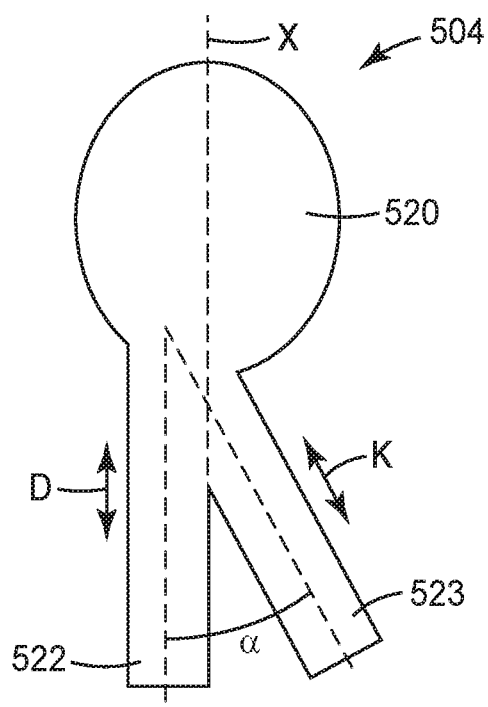
FIGS. 7A-7C each illustrate a coupling layer according to another embodiment of the present disclosure.
Figure 7B:
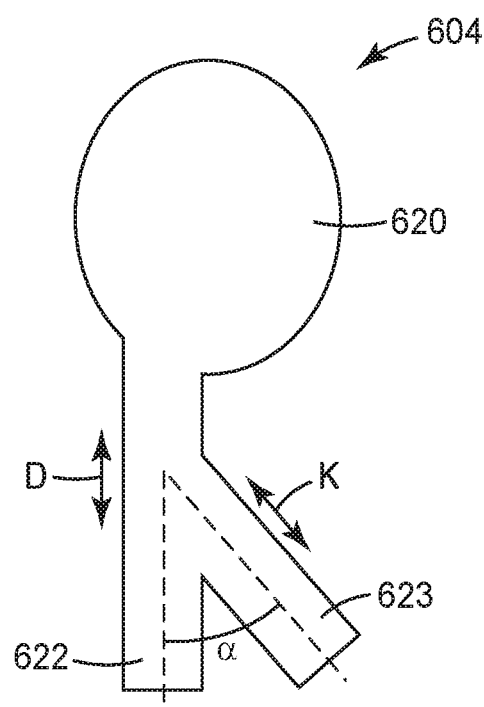
Figure 7C:
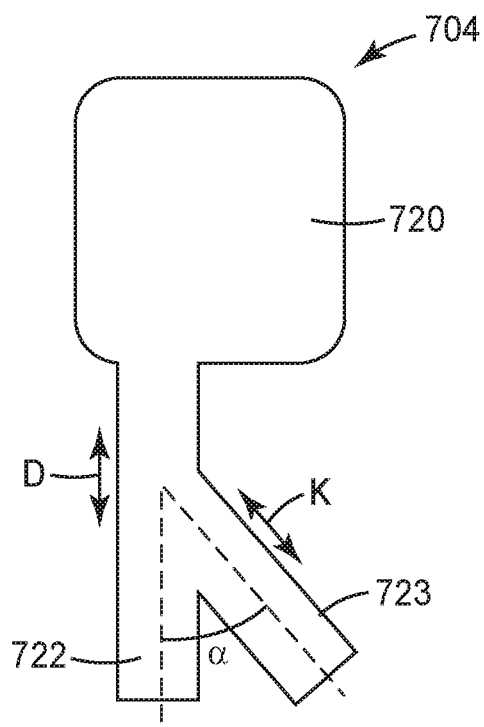

In some embodiments, the coupling layer 104 is generally "R" shaped, or generally has an "R" configuration, i.e., generally takes the shape of a capital English letter "R," as shown in FIGS. 7A-7C, described in greater detail below.

As shown in FIG. 1, in some embodiments, the leg 122 can be linear. Furthermore, in some embodiments, the leg 122 can have a uniform width along its length extending from the first end 120.

The coupling layer 104 can include a first major surface 130 configured to be positioned toward the patient (i.e., toward the patient's skin and nose) and toward a nasogastric tube to be secured by the system 100, and a second major surface 134 configured to face away from the patient (i.e., away from the patient's skin and nose) and the nasogastric tube, the second major surface 134 being opposite the first major surface 130. The coupling layer 104 can include one or more adhesives on the first major surface 130, such as the securing adhesive 132 shown in FIG. 1. For example, in some embodiments, the first major surface 130 can include a different adhesive in the region of the first end 120 than in the region of the leg 122, but this need not be the case. In some embodiments, the first major surface 130 can include first coupling means located at least partially in the first end 120 configured for repositionable coupling to the second major surface 114 of the base layer 102, and second coupling means located at least partially in the leg 122 configured to secure a nasogastric tube. However, in some embodiments, the first major surface 130 of the coupling layer 104 can include one coupling means (e.g., one securing adhesive). In such embodiments, the second major surface 114 of the base layer 102 can be modified to include a release agent (e.g., in the form of a release layer, a release coating, or a combination thereof) configured to release the securing adhesive on the first major surface 130 of the coupling layer 104, such that the first end 120 of the coupling layer 104 is repositionable on the base layer 102 as needed.

In some embodiments, as described below with respect to FIGS. 3A and 3B, a mechanical fastener can be employed (e.g., between the second major surface 114 of the base layer 102 and the first major surface 130 of the first end 120 of the coupling layer 104) in addition to the securing adhesive 132, or as an alternative thereto. For example, one mating surface of a mechanical fastener can be employed on the first major surface 130 of the coupling layer 104, and the complementary mating surface of the mechanical fastener can be employed on the second major surface 114 of the base layer 102 to achieve strong but repositionable coupling between the base layer 102 and the coupling layer 104.

However, even though the first end 120 of the coupling layer 104 (and particularly, the first major surface 130 thereof) and the base layer 102 (and particularly, the second major surface 114 thereof) are configured such that the first end 120 of the coupling layer 104 is repositionable on the base layer 102, the engagement (e.g., adhesion) between the first end 120 of the coupling layer 104 and the base layer 102 also still needs to be sufficiently strong in order to provide reliable securement of a nasogastric tube for the desired period of time.

That is, whether an adhesive, a mechanical fastener, or another coupling means is employed between the base layer 102 and the coupling layer 104 (i.e., the first end 120 thereof), the base layer 102 and the coupling layer 104, and particularly, the second major surface 114 of the base layer 102 and the first major surface 130 of the coupling layer 104, should be configured such that the peel force required to remove (i.e., peel) the coupling layer 104 from the base layer 102 is relatively low to allow easy repositioning as necessary, while the shear strength between the layers is relatively high to ensure adequate securement of the nasogastric tube. The present inventors discovered that by employing base layers and coupling layers specifically shaped and configured as described herein, they were able to achieve this balance of mechanical properties.

As shown in FIG. 1 by way of example only, in some embodiments, the base layer 102 can have a generally triangular shape, and particularly, generally has the shape of an equilateral triangle. The base layer 102 also has rounded corners for enhanced patient comfort. However, the base layer 102 can have any shape that is suitable for covering or wrapping over a nose, and particularly, the top of a nose. In some embodiments, the base layer 102 can have a shape that is suitable for covering a substantial portion of a nose, including the bridge of the nose and at least part of the lateral sides of the nose. Furthermore, in some embodiments, as shown in FIG. 1, the base layer 102 can have lateral symmetry, which can enhance the coupling to a nose. However, generally, the base layer 102 is also shaped so as not to extend downwardly over the tip or the nose or to otherwise interfere with a nasogastric tube to be secured by the system 100.

Figure 5A:
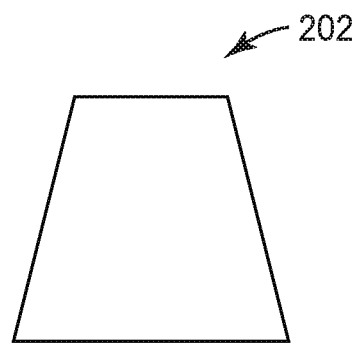
FIGS. 5A and 5B each illustrate a base layer according to another embodiment of the present disclosure.
Figure 5B:
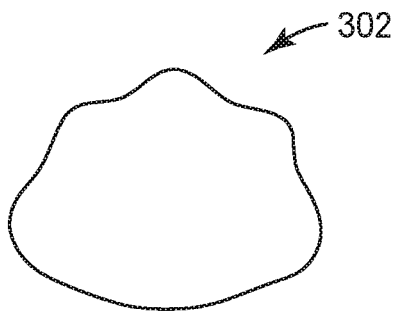

FIGS. 5A and 5B illustrate two examples of alternative shapes for base layers of the present disclosure. FIG. 5A shows a base layer 202 having a generally trapezoidal shape that is wider at its base (i.e., the portion to be positioned toward the tip of the nose) than it is at its top (i.e., the portion to be positioned away from the tip of the nose). FIG. 5B shows a base layer 302 having an irregular lobed shape that is wider at its base than at its top and that includes one or more scalloped rounded edges, which can enhance the conformability of the base layer 302 to a nose and/or patient comfort. While FIGS. 5A and 5B are illustrated to show other possible base layer shapes that can be employed, the three illustrated shapes (i.e., in FIGS. 1, 5A and 5B) are not exhaustive and other shapes that suitably cover the nose are also possible, including, but not limited to, oblong, circular, parallelogrammatic (e.g., square, rectangular), other suitable shapes, or combinations thereof. Any of the previous or following disclosure regarding base layers of the present disclosure refers to the base layer 102 of FIG. 1 for simplicity, but it should be understood that any such disclosure can also equally apply to the base layers 202 and 302 of FIGS. 5A and 5B.

As shown FIG. 1, in some embodiments, the first end 120 of the coupling layer 104 can have a shape that mimics the shape of the base layer 102, while also generally being smaller than the base layer 102, such that the area of the first end 120 can be contained within the area of the base layer 102 when the first end 120 is coupled to the base layer 102. Such a relationship between the shape and size of the first end 120 of the coupling layer 104 and the base layer 102 can enhance the coupling between the first end 120 and the base layer 102. The first end 120 of FIG. 1 has a generally circular shape, and particularly is slightly oblong, such that it is longer in the longitudinal direction D than it is wide in the lateral direction L. However, similar to the base layer 102, the first end 120 of the coupling layer 104 can have any shape suitable for coupling to the base layer 102 and for also covering or wrapping over at least a portion of a nose, and particularly, the top of a nose. In some embodiments, the first end 120 of the coupling layer 104 can have a shape that is suitable for covering a substantial portion of a nose, including the bridge of the nose and at least part of the lateral sides of the nose. Furthermore, in some embodiments, as shown in FIG. 1, the first end 120 can have lateral symmetry (i.e., in the lateral direction L), which can enhance the coupling to a nose. In addition, the coupling layer 104 can be configured to extend down from a bridge of the nose and over the front tip of the nose. Such a configuration can ensure that the nasogastric tube is secured in such a way that limits lateral pulling or tension on the nasogastric tube that could cause pressure ulcers on the nostril.

Figure 6B:
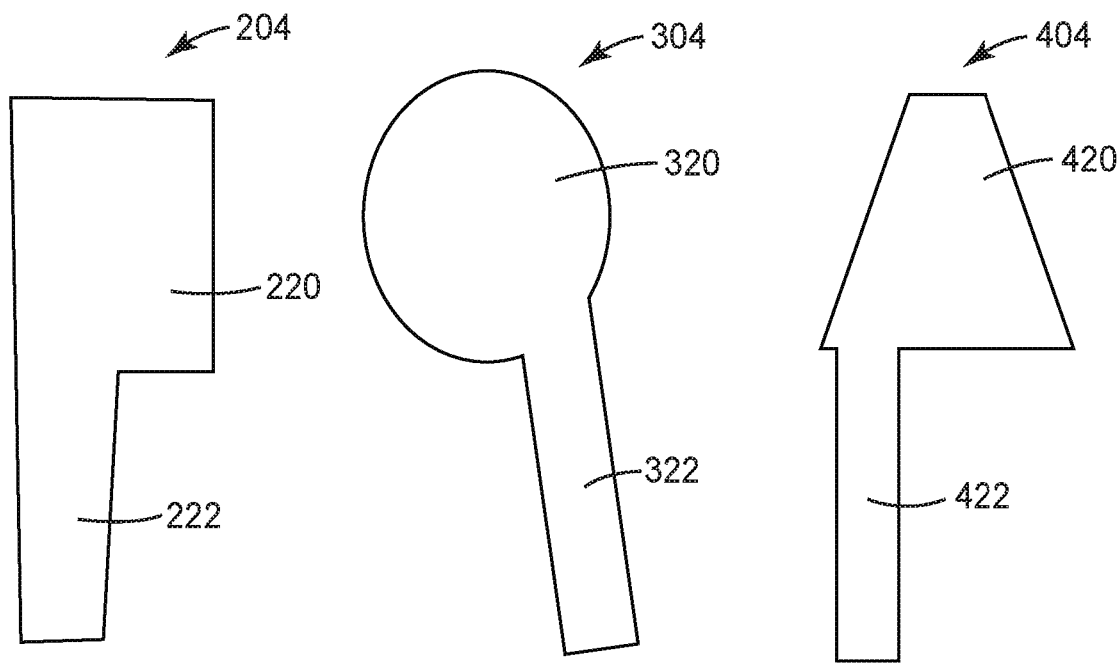
Figure 6C:
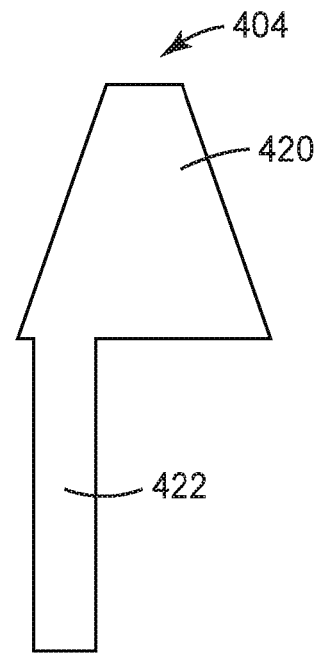

FIGS. 6A-6C illustrate three examples of alternative shapes for coupling layers of the present disclosure. FIG. 6A shows a coupling layer 204 having a generally rectangular first end 220, and a leg 222 extending downwardly therefrom that connects to the first end 220 to the left of a lateral center (i.e., is offset from the lateral center) of the first end 220, generally forming a "p" configuration. Specifically, the leg 222 connects to a left lateral half of a lower end of the first end 220. The leg 222 extends substantially perpendicularly with respect to the bottom edge of the generally rectangular first end 420.

By way of example, the first end 220 has lateral symmetry, and the leg 222 is linear but does not have a uniform width in a longitudinal direction extending from the first end 220. Rather, the leg 222 tapers longitudinally from the location at which it connects to the first end 220 from a width equal to about half the width of the first end 220 to a narrower width at its outermost end. As a result, the leg 222 has a varying width that varies with respect to its longitudinal direction, and by way of example, the leg 222 of FIG. 6A is wider toward the first end 220, and particularly, is widest where the leg 222 connects to the first end 220. Furthermore, the length of the first end 220 and the leg 222 are about equal in the longitudinal direction. Unlike the coupling layer 104 of FIG. 1, the first end 220 does not extend laterally on both sides of the leg 222. Rather, the first end 220 only extends laterally outwardly with respect to the leg 222 on one side of the leg, and particularly, on the right side. While the coupling layer 204 is described as being "p" shaped, it should be understood that a mirror image of the coupling layer 204 can also be employed, generally having a "q" shape.

FIG. 6B shows a coupling layer 304 having a generally circular or oblong first end 320, and a leg 322 extending downwardly therefrom that connects to the first end 320 at a location located to the right of a lateral center (i.e., is offset from the lateral center) of the first end 320, generally forming a "q" configuration. Any disclosure herein regarding the coupling layer 104 of FIG. 1 can equally apply to the coupling layer 304 of FIG. 6B, and vice versa, except that the coupling layer 304 of FIG. 6B has the leg 322 on its right side and is generally "q" shaped, rather than "p" shaped.

FIG. 6C shows a coupling layer 404 having a generally trapezoidal first end 420 that is wider at its base (i.e., the lower end to be positioned toward a tip of a nose), and a leg 422 extending downwardly therefrom that connects to the first end 420 to the left of a lateral center (i.e., is offset from the lateral center) of the first end 420, generally forming a "p" configuration. The leg 422 extends substantially perpendicularly with respect to the bottom edge of the generally trapezoidal first end 420. By way of example, the first end 420 has lateral symmetry, the leg 422 is linear, and the leg 422 is and is generally uniform in width along its length in the longitudinal direction. The first end 420 extends at least partially laterally with respect to the leg 422. While the coupling layer 404 is described as being "p" shaped, it should be understood that a mirror image of the coupling layer 404 can also be employed, generally having a "q" shape.

FIG. 7A illustrates a coupling layer 504 having a generally circular or oblong first end 520; a first leg 522 extending downwardly therefrom that connects to the first end 520 to the left of a lateral center (i.e., is offset from the lateral center) of the first end 520; and a second leg 523 extending outwardly from the first leg 522 at an acute angle α with respect to a longitudinal direction D of the first leg 522 along which the first leg 522 is elongated, generally forming an "R" shape. Specifically, the second leg 523 can be elongated along a longitudinal direction K that is oriented with respect to the longitudinal direction D of the first leg 522 at the acute angle α.

Said another way, in some embodiments, the first end 520 of the coupling layer 504 is laterally symmetrical about a central longitudinal axis X, wherein the first leg 522 connects to the first end 520 at a position that is located laterally with respect to the central longitudinal axis X of the first end 520, wherein the longitudinal direction D of the first leg is substantially parallel to and spaced from the central longitudinal axis X of the first end 520, and wherein the second leg 523 is elongated along a longitudinal direction K that is oriented at an acute angle α with respect to the central longitudinal axis X of the first end 520.

As shown in FIG. 7A, in some embodiments, the second leg 523 can connect to the first end 520 adjacent the location at which the first leg 522 connects to the first end 520. The first leg 522 and the second leg 523 can together enhance the security of a nasogastric tube held by the system. For example, in some embodiments, each of the legs 522 and 523 can be wrapped (e.g., sequentially) about at least a portion of a circumference of a nasogastric tube. In other embodiments, each of the legs 522 and 523 can be configured to be folded over a nasogastric tube and coupled to one another (e.g., via adhesive, mechanical fastener, or other suitable coupling means). In such embodiments, the second major surface 134 of the coupling layer 504, at least in the regions of the first and second legs 522 and 523, can include a release agent (e.g., a low adhesion backsize coating), as described above with respect to the release agent 136 of FIG. 2A.

FIG. 7B illustrates a coupling layer 604 having a generally circular or oblong first end 620; a first leg 622; and a second leg 623 extending outwardly from the first leg 622 at an acute angle α with respect to a longitudinal direction D of the first leg 622 along which the first leg 622 is elongated, generally forming an "R" shape. Specifically, the second leg 623 can be elongated along a longitudinal direction K that is oriented with respect to the longitudinal direction D of the first leg 622 at the acute angle α. The coupling layer 604 is very similar to the coupling layer 504 of FIG. 7A, except that the second leg 623 connects to the first leg 622 at a location along the length of the first leg 622 that is spaced a distance from the first end 620, such that the second leg 623 does not directly connect to the first end 620.

FIG. 7C illustrates a coupling layer 704 having a generally square first end 720 with rounded corners; a first leg 722; and a second leg 723 extending outwardly from the first leg 722 at an acute angle α with respect to a longitudinal direction D of the first leg 722 along which the first leg 722 is elongated, generally forming an "R" shape. Specifically, the second leg 723 can be elongated along a longitudinal direction K that is oriented with respect to the longitudinal direction D of the first leg 722 at the acute angle α. The coupling layer 704 is substantially the same as the coupling layer 604 of FIG. 7B, except that the first end 720 is substantially square.

While FIGS. 7A-7C each illustrate coupling layers having an "R" configuration, it should be understood that the coupling layers can instead have the mirror image configuration of what is shown in FIGS. 7A-7C, generally forming a backwards or reverse "R" configuration. In addition, while two legs are illustrated in the coupling layers 504, 604 and 704 of FIGS. 7A-7C, it should be understood that as many legs as structurally possible can be employed without overly hindering nasogastric tube securement or adding unnecessary complexity. In some embodiments, two legs extending at least partially downwardly but separated by the acute angle α can be preferred.

While FIGS. 6A-7B are illustrated to show other possible coupling layer shapes that can be employed, the seven illustrated shapes (i.e., in FIGS. 1, 6A-6C and 7A-7C) are not exhaustive and other shapes, or other combinations of first end shapes and leg configurations are also possible to provide suitable coupling between the first end of the coupling layer and the base layer while also providing sufficient coupling between the one or more legs and a nasogastric tube. Thus, various shapes can be employed as the first end, including, but not limited to, trapezoidal, lobed, triangular, oblong, circular, parallelogrammatic (e.g., square, rectangular), other suitable shapes, or combinations thereof. Any of the previous or following disclosure regarding coupling layers of the present disclosure refers to the coupling layer 104 of FIG. 1 for simplicity, but it should be understood that any such disclosure can also equally apply to the coupling layers 204, 304 and 404 of FIGS. 6A-6C, as well as the coupling layers 504, 604 and 704 of FIGS. 7A-7C.

With continued reference to FIG. 1, in some embodiments, the base layer 102 can have a footprint area A, which is measured when the base layer 102 is in a flat configuration as shown in FIG. 1, e.g., before being applied to a nose. This area A is the overall footprint that the base layer 102 takes up on the release liner 103 and generally over a nose, when in use. The first end 120 of the coupling layer 104 can have a footprint area B. In some embodiments, the footprint area B of the first end 120 can be at least 0.3 A (i.e., at least 30% of footprint area A); in some embodiments, at least 0.4 A; in some embodiments, at least 0.5 A; in some embodiments, at least 0.6 A; in some embodiments, at least 0.7 A; in some embodiments, at least 0.75 A; in some embodiments, at least 0.8 A; in some embodiments, at least 0.85 A; in some embodiments, at least 0.9 A; and in some embodiments, at least 0.95 A. In some embodiments, the footprint area B of the first end 120 can be no greater than 0.98 A; in some embodiments, no greater than 0.97 A; in some embodiments, no greater than 0.95 A. Increasing the footprint area B of the first end 120 of the coupling layer 104, relative to the footprint area A of the base layer 102, can enhance the coupling (e.g., shear strength) between the first end 120 and the base layer 102, which can enhance the securement of a nasogastric tube.

Figure 2A:
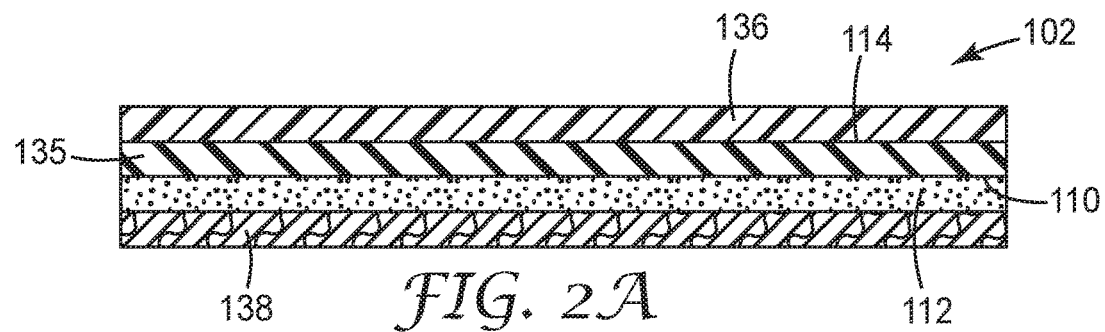
FIG. 2A is a side cross-sectional view of the base layer of the system of FIG. 1 according to one embodiment of the present disclosure, taken along line 2A-2A of FIG. 1.

As shown in FIG. 2A which illustrates a side cross-sectional view of one embodiment of the base layer 102, in some embodiments, the base layer 102 can include a backing 135 that provides the first major surface 110 and the second major surface 114. In some embodiments, the base layer 102 can include a multi-layer structure, including a plurality of backings 135, and can optionally include additional adhesives located between adjacent backings 135. In such embodiments, the first major surface 110 of the base layer 102 can be provided by a lowermost backing, and the second major surface 114 of the base layer 102 can be provided by an uppermost backing in the multi-layer structure. That is, while only one backing 135 is shown in FIG. 2A, it should be understood that as many backings 135 (and, optionally, adhesives therebetween) can be employed in the base layer 102, as long as the exposed adhesive on the first major surface 110 of the overall base layer 102 is a skin-contact adhesive 112 suitable for being adhered to skin, and particularly to the skin on the nose. Various additional details regarding backings of the present disclosure are described in greater detail below under the section entitled, "Backings."

In addition, in some embodiments, the multi-layer concept can also be used in the configuration of the kit 101 of FIG. 1, where, for example, the base layer 102 and the coupling layer 104 can be provided already overlapped on the release liner 103 (e.g., where a release agent on a top surface of one layer can serve as the release liner for another layer). In addition, or alternatively, in some embodiments, the kit 101 can optionally include an extra coupling layer 104 that can be supplied to guarantee an extra adjustment, if necessary, for a nasogastric tube. In some embodiments, the additional coupling layer 104, for example, can be supplied directly under the first coupling layer 104, thereby taking up no additional footprint area of the kit 101. Furthermore, in some embodiments, the first tape strip 106 and the second tape strip 108 can be provided in an overlapped configuration on the release liner 103. The cross-sectional multilayer configuration of such overlapped embodiments would be similar to the construction shown in FIG. 2B, which is described in greater detail below. Furthermore, in some embodiments, the kit 101 can include multiple coupling layers 104 of different shapes, types and/or sizes, such that the kit 101 provides several options for use, for example, depending on patient anatomy.

As shown in FIG. 2A, the base layer 102 can further include the skin-contact adhesive 112 on the first major surface 110, and a release agent (e.g., a release coating) 136 on the second major surface 114 of the backing 135. Such a release agent 136 can be selected to function as a release layer or liner for an adhesive (e.g., a securing adhesive) located on the first major surface 130 of the coupling layer 104, and particularly, for an adhesive located on the first major surface 130 in the first end 120 of the coupling layer 104. As further shown in FIG. 2A, in some embodiments, the base layer 102 can further include a release liner 138 (e.g., a paper liner comprising a release agent, e.g., silicone, for the skin-contact adhesive 112). However, in some embodiments, as shown in FIG. 1, the base layer 102 may be provided on the same release liner 103 as the rest of the system 100 and not include its own dedicated release liner 138.

In some embodiments, the release agent 136 can include a low adhesion (low adhesion backsize, or LAB) coating provided on the second major surface 114 of the base layer 102 at least in a region positioned to come into contact with the coupling layer 104. The low adhesion coating can allow the coupling layer 104 to be repositionable on the base layer 102 to the extent necessary. A description of a low adhesion backing material suitable for use with medical dressings of the present disclosure can be found in U.S. Pat. Nos. 5,531,855 and 6,264,976, which are incorporated herein by reference in their entirety.

In some embodiments, the backing 135 can be formed of a stretchable material (e.g., a stretchable nonwoven, woven, film, or combination thereof) that can provide gentle removal to minimize skin damage when the system 100

(and, particularly, the base layer 102 of the system 100) is removed. For example, in some embodiments, the base layer 102 can include a stretch release backing 135 (i.e., a backing 135 formed of a stretch release material) and skin-contact adhesive 112, such that while stretching, there is a distribution of tension force between the backing 135, the adhesive 112, and the skin, providing adhesive failures and reducing the tension applied on the skin as the base layer 102 is removed.

By way of example only, in some embodiments, the backing 135 and the skin-contact adhesive 112 can be provided by polyurethane stretchable nonwoven tape, such as the tape available as 3M™ CoTran™ 9699 Melt Blow Polyurethane Tape from 3M Company, St. Paul, Minn., any of the materials A-H of Table 1 in the Examples section below, other suitable tapes/backings, or a combination thereof.

In some embodiments, it can be advantageous for the base layer 102 to be formed of a relatively stretchy (e.g., elastic, viscoelastic, etc.) and conformable material, while the coupling layer 104 is formed of a relatively non-stretchy (e.g., inelastic, rigid, etc.) material. Such relative material properties can enhance patient comfort and/or facilitate removal of the base layer 102 from the skin, while also ensuring enough tensile strength in the coupling layer 104 to securely hold a nasogastric tube in a desired position without allowing the nasogastric tube to shift or cause undue pressure on the skin or nostril.

For example, in some embodiments, the base layer 102 can have a percent elongation at break (or maximum elongation) of at least 200%; in some embodiments, at least 250%; in some embodiments, at least 300%; in some embodiments, at least 400%; and in some embodiments, at least 500%.

In some embodiments, the coupling layer 104 can have a percent elongation at break of no greater than 100%; in some embodiments, no greater than 80%; in some embodiments, no greater than 75%; and in some embodiments, no greater than 50%.

Percent elongation at break can be measured using any standard tensile testing equipment known to those of ordinary skill in the art. One example of tensile testing is described in the Examples section.

Figure 2B:
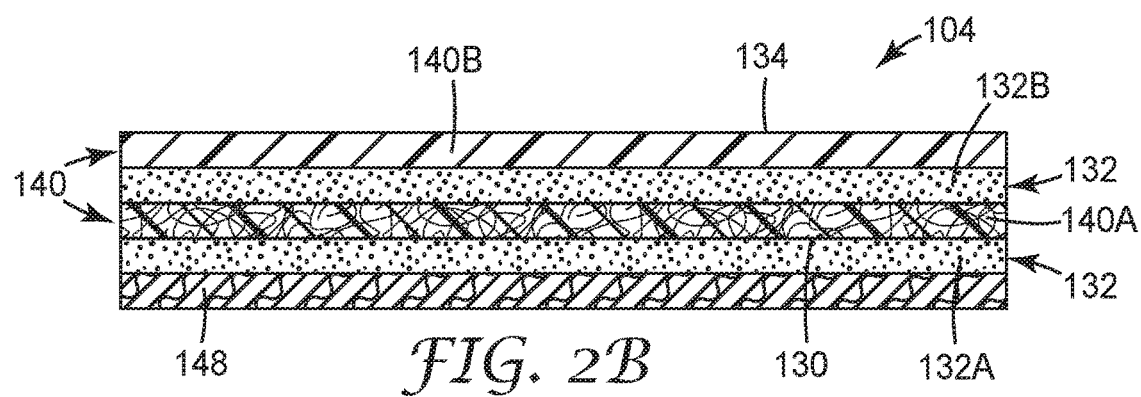
FIG. 2B is a side cross-sectional view of the coupling layer of the system of FIG. 1 according to one embodiment of the present disclosure, taken along line 2B-2B of FIG. 1.

As shown in FIG. 2B, in some embodiments, the coupling layer 104 can include a multi-layer structure (e.g., multi-layer tape or multiple tapes) comprising one or more backings 140 and one or more securing adhesives 132. As shown in FIG. 2B, the first major surface 130 of the coupling layer 104 can be provided by one backing 140, and the first major surface 130 can include a securing adhesive 132 configured to repositionably adhere to the release agent 136 on the second major surface 114 of the base layer 102, as well as adhere to a nasogastric tube (and, optionally, its own second major surface 134) to securely hold a nasogastric tube in place. By way of example only, in the embodiment illustrated in FIG. 2B, the first major surface 130 is provided by a first adhesive backing (e.g., tape) 140A, and the second major surface 134 is provided by a second adhesive backing (e.g., tape) 140B that is laminated over the first adhesive backing 140A. However, it should be understood that the illustrated laminate structure need not be employed and that the first major surface 130 and the second major surface 134 can be provided by one backing 140. While two backings 140 and securing adhesives 132 are shown in FIG. 2B by way of example, it should be understood that as few as one backing 140 and securing adhesive 132, or as many as structurally possible or necessary, can be employed.

That is, as shown in FIG. 2B, in some embodiments, the coupling layer 104 can be formed of the first backing 140A and a first securing adhesive 132A, and the second backing 140B and a second securing adhesive 132B that adheres the second backing 140B to the first backing 140A. By way of example only, in some embodiments, the first backing 140A and the first securing adhesive 132A can be provided by a polyethylene terephthalate (PET) nonwoven-acrylic adhesive tape, such as the tape available as 3M™ Tan Spunlaced Nonwoven Medical Tape 9916, 3M Company, St. Paul, Minn. In addition, in some embodiments, the second backing 140B and the second securing adhesive 132B can be provided by a polyethylene backing-acrylic adhesive tape, such as the tape available as 3M™ Blenderm™ Surgical Tape 1525, 3M Company, St. Paul, Minn. Such a laminate structure can provide the necessary strength to the coupling layer 104 to secure a nasogastric tube and keep it in the correct position for the desired period of time. The first securing adhesive 132A functions as the exposed securing adhesive that will be adhered to the nasogastric tube. The specific tapes listed above are described by way of example; however, the coupling layer 104 can also include any of the materials I-M of Table 1 in the Examples section below, other suitable tapes/backings, or a combination thereof.

As further shown in FIG. 2B, the coupling layer 104 can further include a release liner 148 (e.g., a paper liner comprising release agent for the securing adhesive 132 exposed on the first major surface 130). However, in some embodiments, as shown in FIG. 1, the coupling layer 104 may be provided on the same release liner 103 as the rest of the system 100 and not include its own dedicated release liner 148.

Furthermore, in some embodiments, the second major surface 134 of the coupling layer 104 can include a release agent similar to the release agent 136 of the base layer 102 of FIG. 2A, described above. For example, the second major surface 134 can include a low adhesion (low adhesion backsize, or LAB) coating. Such a release agent on the second major surface 134 of the coupling layer 104 (e.g., at least in the region of one or more legs of the coupling layer 104) can facilitate unwrapping the coupling layer 104 during the process of removing the system 100 and decoupling the system 100 from a nasogastric tube.

While only one securing adhesive 132 is shown as being present on the first major surface 130 of the coupling layer 104, it should be understood that in some embodiments, the first major surface 130 of the coupling layer 104 in at least a portion of the first end 120 can include a first securing adhesive (e.g., a less aggressive adhesive with a lower peel force on the second major surface 114 of the base layer 102), and the first major surface 130 in at least a portion of the leg 122 can include a second securing adhesive (e.g., a more aggressive adhesive with a higher peel force on the outer surface of the nasogastric tube) that is different from the first securing adhesive.

Furthermore, while the base layer 102 shown in FIG. 2A is shown as being the same size (i.e., length) as the coupling layer 104 of FIG. 2B, these two figures are not necessarily drawn to scale. Rather, as shown in FIG. 1, the coupling layer 104 would generally be longer than the base layer 102 (i.e., in the direction of the width of the page of FIGS. 2A and 2B), such that the first end 120 of the coupling layer 104 can be sized and positioned to overlap at least a portion of the base layer 102, while the leg 122 can extend beyond the area of the base layer 102 to access and secure a nasogastric tube, e.g., according to the relative sizes shown in FIG. 1.

Figure 3A:
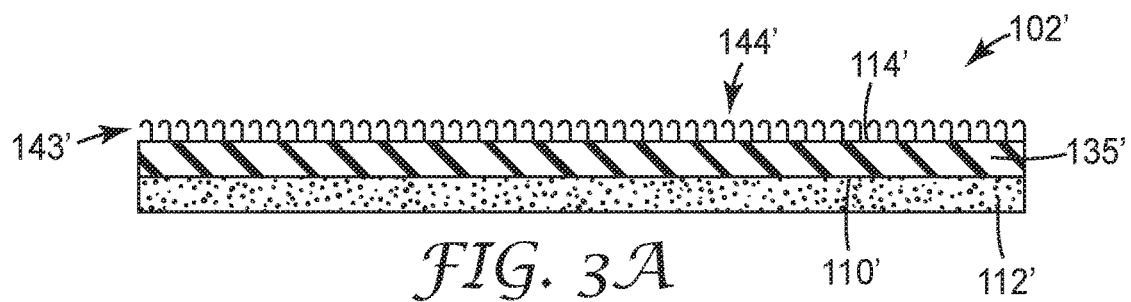
FIG. 3A is a side cross-sectional view of the base layer of the system of FIG. 1 according to another embodiment of the present disclosure.
Figure 3B:
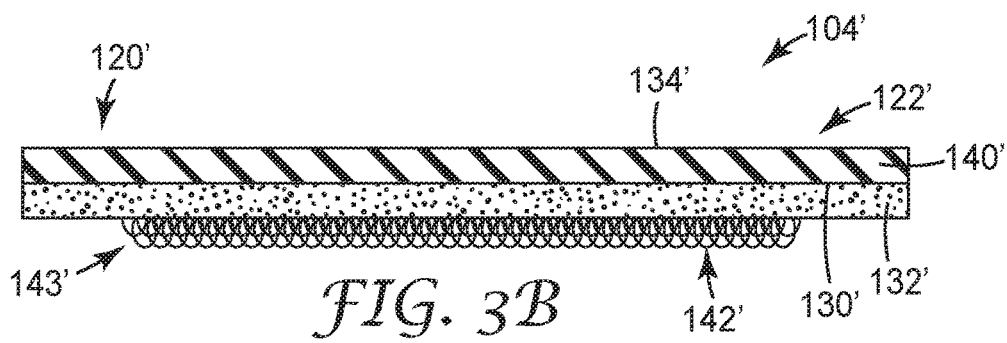
FIG. 3B is a side cross-sectional view of the coupling layer of the system of FIG. 1 according to another embodiment of the present disclosure.

FIGS. 3A and 3B illustrate a base layer 102' and a coupling layer 104', respectively, according to another embodiment of the present disclosure. For simplicity, no additional release liners are shown in FIGS. 3A and 3B. In addition, each of the base layer 102' and the coupling layer 104' are shown for simplicity as including only one backing—backings 135' and 140', respectively. However, it should be understood that one or both of the base layer 102 and the coupling layer 104 can be a multi-layer structure, as described above and as shown in FIG. 2B.

FIGS. 3A and 3B represent an example of repositionable coupling means between the base layer 102' and the coupling layer 104' that includes a mechanical fastener. As shown in FIG. 3A, the base layer 102' includes the backing 135' having first major surface 110' and second major surface 114', and a skin-contact adhesive 112' on the first major surface 110'. As shown in FIG. 3B, the coupling layer 104' includes the backing 140' having first major surface 130' and second major surface 134', and a securing adhesive 132' on the first major surface 130'. The coupling layer 104' further includes a first mating surface 142' of a mechanical fastener 143' on the first major surface 130', which can be coupled (e.g., laminated) to the first major surface 130' via the securing adhesive 132'. By way of example only, the first mating surface 142' of the coupling layer 104' is shown as being formed of loops or pile, however, other mechanical fastener features can be used.

As further shown in FIG. 3A, the base layer 102' further includes a second mating surface 144' of the mechanical fastener 143' on the second major surface 114' that is configured to reversibly engage the first mating surface 142' of the coupling layer 104'. By way of example only, the second mating surface 144' is shown as being formed of hooks, however, other mechanical fastener features can be used. In some embodiments, the second mating surface 144' of the mechanical fastener 143' can be provided on the base layer 102' by laminating.

By way of example only, in some embodiments the backing 135' and skin-contact adhesive 112' can be provided by a polyethylene terephthalate (PET)-acrylic adhesive tape, available under the trade designation 3M™ Spunlaced Polyester Nonwoven Medical Tape 1776 from 3M Company, St. Paul, Minn. Other examples useful for providing the backing 135' and the skin-contact adhesive 112', include, but are not limited to, a polyethylene terephthalate (PET) nonwoven-acrylic adhesive tape, such as the tape available as 3M™ Tan Spunlaced Nonwoven Medical Tape 9916 from 3M Company, St. Paul, Minn.; a rayon nonwoven tape, such as the tape available as 3M™ Microporous Tan Rayon Nonwoven Medical Tape 1533 from 3M Company, St. Paul, Minn.; a suitable elastic backing with a gentle adhesive; or a combination thereof.

While the second mating surface 144' is shown as being coextensive with the second major surface 114' of the base layer 102', this need not be the case. Rather, in some embodiments, the second mating surface 144' can have an area less than a total surface area of the second major surface 114', e.g., such that the base layer 102' includes a border around all edges of the second major surface 114' that is free of the second mating surface 144'. Such embodiments can inhibit the potentially harder and more rigid mechanical fastener 143' component from irritating the skin on the nose, by providing a buffer all around where the backing 135' is free of the second mating surface 144'.

As shown in FIG. 3B, in some embodiments, the first mating surface 142' may not be coextensive with the first major surface 130' of the coupling layer 104'. For example, in some embodiments, the securing adhesive 132' may be exposed in a portion of the first end 120' (e.g., in some embodiments, in an area accounting for less than 10% of the total area of the first major surface 130' of the first end 120', in some embodiments, less than 20%, or in some embodiments, less than 30%). This can reduce the risk of the coupling layer 104' being inadvertently removed from the base layer 102' during use, enhancing the coupling between the first end 120' of the coupling layer 104' and the base layer 102', while still allowing for repositioning of the coupling layer 104' on the base layer 102' as needed. In some embodiments, however, the entire first end 120' of the coupling layer 104' can include the first mating surface 142' of the mechanical fastener 143' (e.g., if the mechanical fastener 143' has a sufficiently aggressive engagement between the first mating surface 142' and the second mating surface 144').

Furthermore, as shown in FIG. 3B, at least a portion of the leg 122' can be free of the mechanical fastener 143', so that the securing adhesive 132' can be exposed for securing a nasogastric tube. In some embodiments, at least 80% of the leg 122' is free of the mechanical fastener 143', in some embodiments, at least 90%, and in some embodiments, at least 95%.

Methods of Using Systems of the Present Disclosure to Secure a Nasogastric Tube

FIGS. 4A-4J illustrate a method of securing a nasogastric tube using the nasogastric tube securement system 100 of FIG. 1. Before inserting a nasogastric tube T into a subject's nose, the length of the tube to be inserted to reach a desired depth can be measured. Then, the first tape strip 106 can be wrapped about a nasogastric tube T (e.g., about a circumference thereof) to mark the measured length, e.g., by adhering the securing adhesive 107 to the outer surface of the nasogastric tube T and continuing to wrap the first tape strip 106 over itself. Then, as shown in FIG. 4A, the nasogastric tube T can be inserted into a nostril to the desired depth (see FIG. 4B).

As shown in FIG. 4B, the base layer 102 can be applied to the subject's nose, i.e., to cover a substantial portion of the top surface of the nose. Particularly, the skin-contact adhesive 112 on the first major surface 110 of the base layer 102 can be adhered to the skin on the top of the nose.

As shown in FIG. 4C, the first end 120 of the coupling layer 104 can then be applied to the base layer 102. As shown in FIG. 4C, the securing adhesive 132 can be used to adhere the first major surface 130 of the first end 120 of the coupling layer 104 to the second major surface 114 of the base layer 102. Alternatively or additionally, as shown in FIGS. 3A and 3B, the first mating surface 142' of the mechanical fastener 143' on the first major surface 130' of the coupling layer 104' can be engaged with the second mating surface 144' on the second major surface 114' of the base layer 102'. The first end 120 of the coupling layer 104 can be positioned on the base layer 102 in such a way that the first end 120 is positioned predominantly within the area of the base layer 102 and is generally aligned with the base layer 102.

Figure 4D:
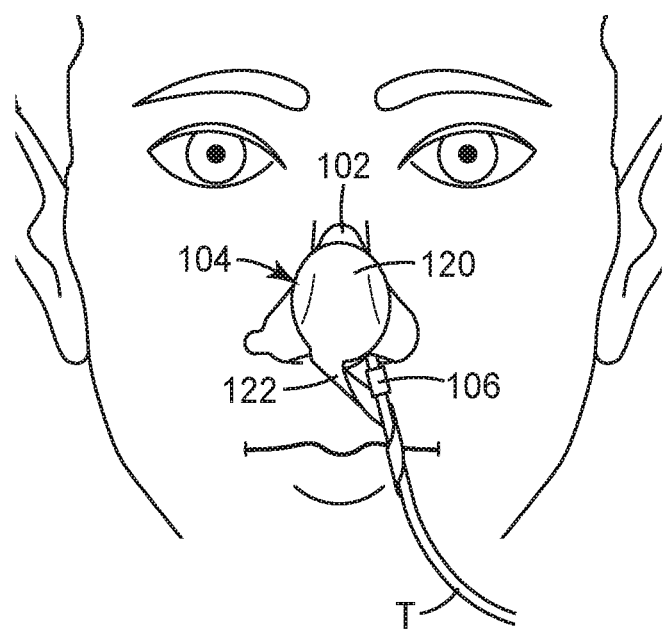

As shown in FIGS. 4C and 4D, the first major surface 130 of the leg 122 (or plurality of legs, if more than one leg is employed, as shown in FIGS. 7A-7C) can be positioned in contact with at least a portion of the nasogastric tube by wrapping (e.g., spiraling) the leg 122 around the nasogastric tube, with the first major surface 130 toward the nasogastric tube. In some embodiments, the leg 122 can be secured to the nasogastric tube T and optionally also to its second major surface 134. Alternatively, in embodiments employing more than one leg, the legs can be folded toward one another (e.g., first major surfaces 130 toward one another) over the nasogastric tube T and secured to one another about the nasogastric tube T, e.g., by adhesive, mechanical fastener, or another suitable coupling means. In such embodiments, the legs can be coupled (e.g., adhered) to the nasogastric tube as well as to each other.

Figure 4E:
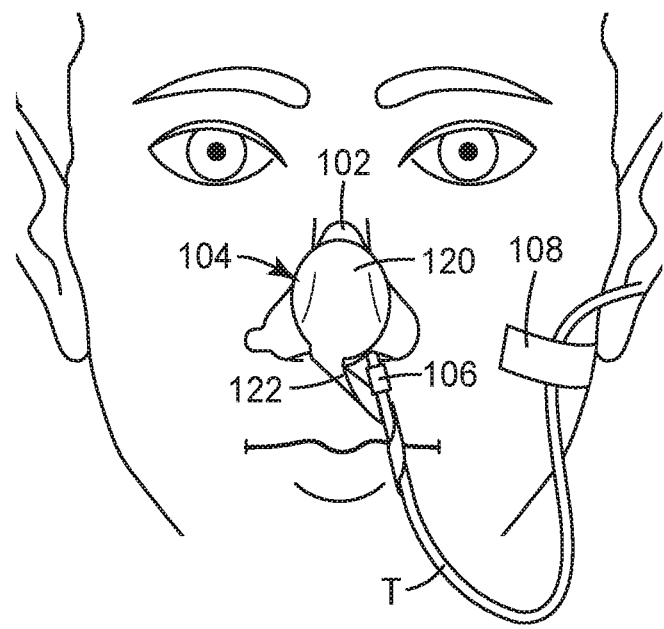

As shown in FIG. 4E, the second tape strip 108 can be used to adhere excess length of the nasogastric tube T to the patient's skin (e.g., face) in such a way that keeps the nasogastric tube T out of the way and inhibits unnecessary tensions or pulling forces on the nasogastric tube T. The remainder of the nasogastric tube T can then be threaded behind the patient's ear.

Figure 4F:
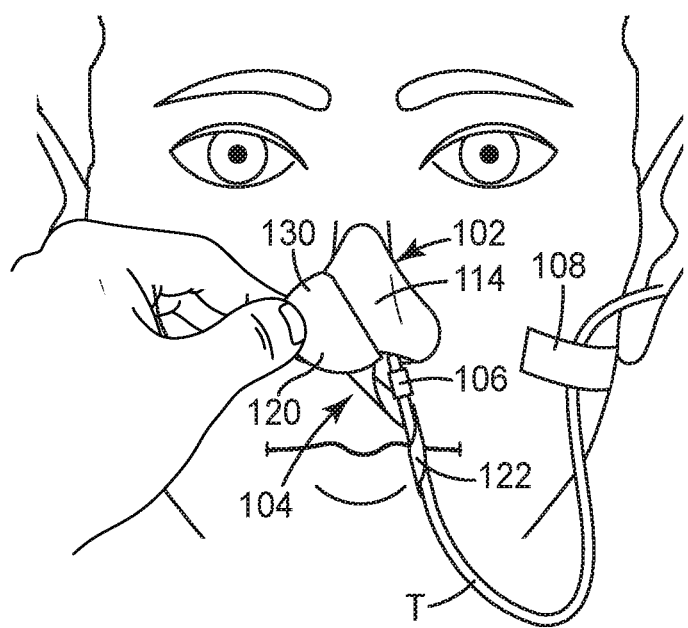
Figure 4G:
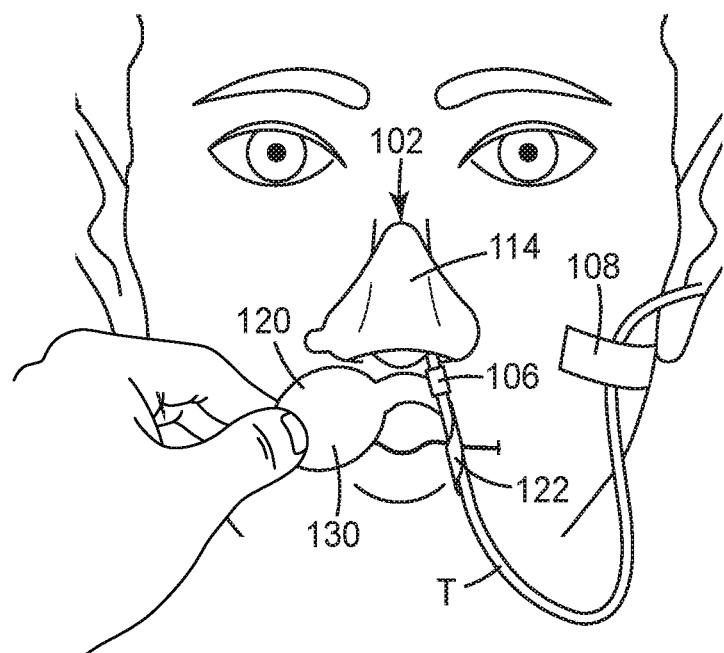

The system 100 as shown in FIG. 4E is therefore fully secured and can remain as shown until repositioning of the coupling layer 104 is necessary or until the system 100 needs to be removed or changed. FIGS. 4F and 4G illustrate how the first end 120 (and particularly, the first major surface 130 thereof) can be repositionable on the second major surface 114 of the base layer 102 while the rest of the coupling layer 104 remains in place on the nasogastric tube T and undisturbed. The first end 120 can then be readjusted as necessary (e.g., to remove any pressures on a nostril) and replaced back on the base layer 102.

Figure 4H:
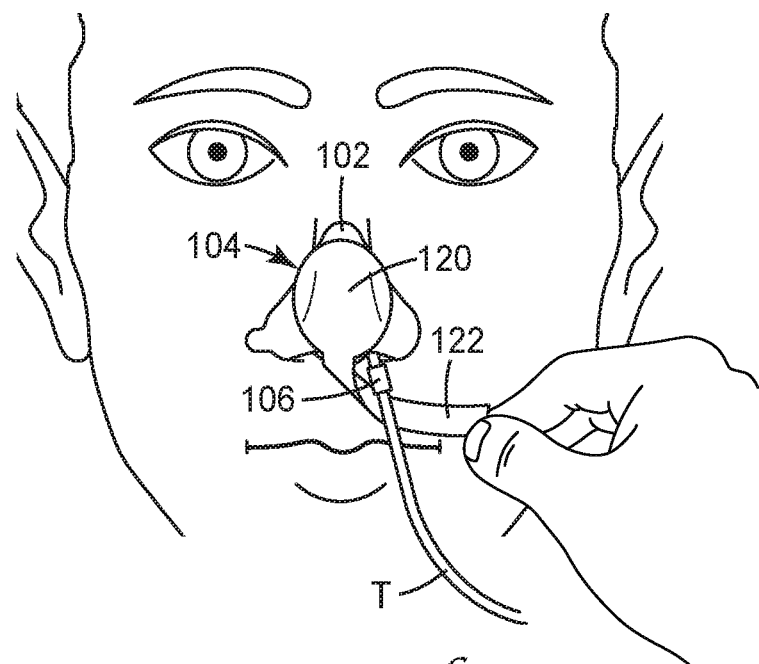
Figure 4I:
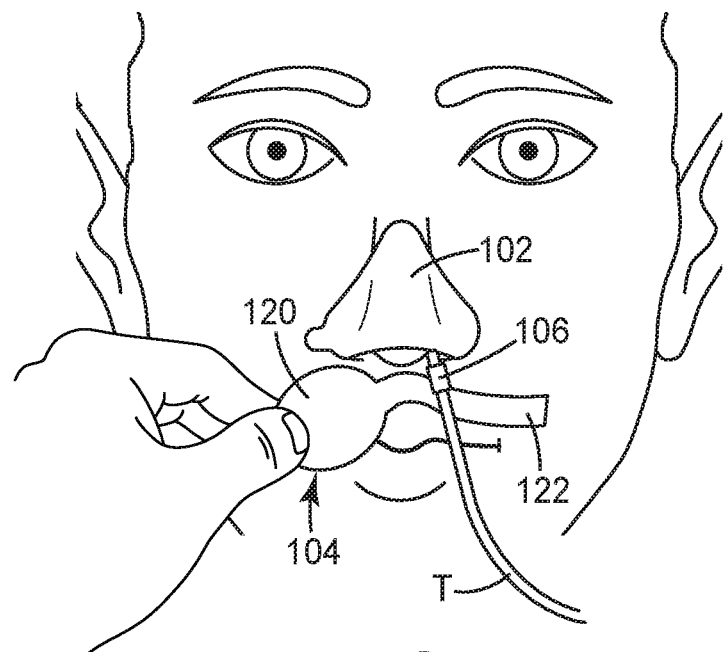
Figure 4J:
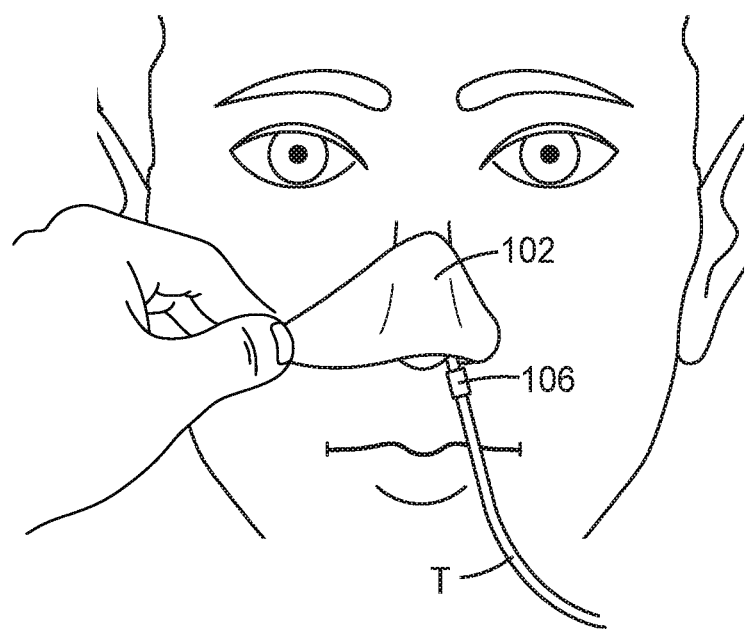

FIGS. 4H-4J illustrate how the system 100 can be removed, e.g., when it is desired to remove the nasogastric tube T. First, if employed, the second tape strip 108 can be peeled from the patient's skin. Then, as shown in FIG. 4H, a portion of the leg 122 can be grasped, and the leg 122 can be unwrapped from around the nasogastric tube T. As shown in FIG. 4I, the first end 120 of the coupling layer 104 can be lifted off of the base layer 102, and the whole coupling layer 104 can be removed (and disposed). While removing the leg 122 first can provide a less cumbersome removal method for removing the coupling layer 104, the first end 120 can be removed first instead. As shown in FIG. 4J, then only the base layer 102 remains on the nose. Then, in embodiments employing a stretch release material in the base layer 102, a corner or edge of the base layer 102 can be grasped, as shown in FIG. 4J, and pulled in order to gently remove the base layer 102 from the nose, reducing the risk of skin damage and increasing patient comfort. In embodiments not employing stretch release material in the base layer 102, the base layer 102 can be simply peeled from the nose.

Backings

Suitable backings for base layers and coupling layers of the present disclosure can include, but are not limited to, one or more of a fabric, a woven fibrous web, a nonwoven fibrous web, a knit, a polymeric film, other familiar dressing materials, or combinations thereof. In some embodiments, the backing materials can include polymeric elastic films (e.g., transparent or non-transparent), and can include, but are not limited to, films formed of elastomeric polyurethanes, co-polyesters, polyethylenes, or combinations thereof. The backing can be a high moisture vapor permeable film, i.e., a backing with a relatively high moisture vapor transmission rate (MVTR). U.S. Pat. No. 3,645,835 describes methods of making such films and methods for testing their permeability. The backing can be constituted of natural or synthetic sources of raw materials.

The backings of the present disclosure advantageously should transmit moisture vapor at a rate equal to or greater than human skin. In some embodiments, the backing can be adhesive-coated. In such embodiments, the adhesive-coated backing can transmit moisture vapor at a rate of at least 300 g/m$^2$/24 hrs/37° C./100-10% RH, and in some embodiments, at least 700 g/m$^2$/24 hrs/37° C./100-10% RH. The backing is generally conformable to anatomical surfaces. As such, when the backing is applied to an anatomical surface, such as a nose, it conforms to the surface even when the surface is moved.

The backing can be a flexible material. For example, the backing can be a film, paper, woven, knit, foam, nonwoven material, or a combination thereof, or one or more layers of film, paper, woven, knit, foam, nonwoven, or a combination thereof. In some embodiments, it can be desirable that at least a portion of the backing is formed of a transparent material to allow for viewing of underlying skin, a medical device, and/or a target site.

By way of example only, in some embodiments, the backing of a base layer of the present disclosure can be formed of a film available under the trade designation TEGADERM® from 3M Company, St. Paul, Minn.

Release Liners

Release liners suitable for use with the systems of the present disclosure can include, but are not limited to, kraft papers, polyethylene, embossed polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can also be employed in the systems of the present disclosure. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films, commercially available from H. P. Smith Co., and fluoropolymer coated polyester films, commercially available from 3M Company (St. Paul) under the brand "SCOTCHPAK™" release liners.

Adhesives

As described above, the securing adhesives of the present disclosure (e.g., the securing adhesive 132 or 107 of FIG. 1 configured to be adhered a nasogastric tube) can have an adhesion that is higher than the skin-contact adhesives of the present disclosure (e.g., the skin-contact adhesive 112 or 109 of FIG. 1). In some embodiments, the securing adhesive and the skin-contact adhesive may be of the same or similar classes of adhesive, but have different adhesion levels. For example, the securing adhesive and/or the skin-contact adhesive may be an acrylate, silicone, urethane, hydrogel, hydrocolloid, natural rubber, or synthetic rubber. Adhesion can also be tuned through changes in adhesive composition, adhesive thickness, or adhesive surface area (e.g., by employing a pattern-coated adhesive).

"Adhesion" refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04 (2010). In some embodiments, adhesion can be defined by shear adhesion using ASTM D3654M-06 (2011). Adhesion is dependent on the specific substrate being adhered to, as well as the time the pressure-sensitive adhesive (PSA) is allowed to dwell on the substrate.

For example, typical peel adhesion values exhibited by pressure-sensitive adhesives in medical dressings maybe in the range of 20 to 300 g/cm as measured from stainless steel. In some embodiments, at least 10% higher peel adhesion, as measured by ASTM D3330/D3330M-04 (2010), of the securing adhesive over the skin-contact adhesive may realize the benefit of both securing to a nasogastric tube, while providing gentle adhesion to the skin.

In some embodiments, the securing adhesive can be an acrylate adhesive and the skin-contact adhesive can be a silicone adhesive. The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain at least some acrylate monomers and may contain additional co-monomers.

Acrylate adhesives are well suited for securing adhesive dressings to medical articles (e.g., nasogastric tubes), or skin. The adhesion can be manipulated to have high adhesion or low adhesion. Generally, the adhesion between acrylate adhesives and another material will increase over time. This property makes acrylate adhesives well suited as the securing adhesive which is intended to secure a nasogastric tube.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate:acrylamide copolymer. Another acrylate adhesive is a 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane (—$SiR_2O$—) repeating units. The silicone-based polymers may be segmented copolymers or polysiloxanes polymers. The terms silicone and siloxane are used interchangeably.

Generally, silicone adhesives are able to effectively secure dressings and tape to skin and upon removal from the skin produce little or no skin damage. Typically, silicone adhesives do not adhere well to polymer-based substrates, like tubing or hardgoods, for example that are often present in nasogastric tubes. Thus, lack of strong adhesion to medical devices/tubing combined with the gentle removal of silicone adhesives from skin make these adhesives well suited as the skin-contact adhesive of the present disclosure.

Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350. Other examples of suitable silicone adhesives are disclosed in PCT Publications WO2010/056541, WO2010/056543 and WO2010/056544, the disclosures of which are incorporated herein by reference.

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348 (now U.S. Pat. No. 7,947,366), the disclosures of which are incorporated herein by reference. Each of the securing or skin-contact adhesive can optionally be applied in a discontinuous manner.

Each embodiment shown in the figures is illustrated as a separate embodiment for clarity in illustrating a variety of features of the nasogastric tube securement systems of the present disclosure. However, it should be understood that any combination of elements and features of any of the embodiments illustrated in the figures and described herein can be employed in the nasogastric tube securement systems of the present disclosure.

In addition, various other features and elements can be employed in the nasogastric tube securement systems of the present disclosure, such as those disclosed in co-pending U.S. Application Nos. 62/208,055; 62/208,060; 62/208,065; and 62/208,069, each of which is incorporated herein by reference in its entirety.

The following embodiments are intended to be illustrative of the present disclosure and not limiting.

Embodiments

1. A nasogastric tube securement system, the system comprising:
   a base layer configured to be adhered to a nose, the base layer having a first major surface comprising a skin-contact adhesive and a second major surface opposite the first major surface; and
   a coupling layer comprising
      a first end comprising coupling means configured to be repositionably coupled to the second major surface of the base layer, and
      a leg connected to and extending from the first end, the leg being elongated along a longitudinal direction, the leg being configured to secure a nasogastric tube;
      wherein the leg connects to the first end at a position that is located toward a lateral side of the first end, relative to a lateral center of the first end; and
      wherein the first end is wider than the leg in a lateral direction that is oriented substantially perpendicularly with respect to the longitudinal direction.

2. The system of embodiment 1, wherein the base layer has a footprint area of A, and wherein the first end has a footprint area of at least 0.3 A.

3. The system of embodiment 1 or 2, wherein the first end of the coupling layer is symmetrical about the lateral center.

4. The system of any of embodiments 1-3, wherein the leg of the coupling layer connects to the first end of the coupling layer at a location that is not a lateral center of the first end.

5. The system of any of embodiments 1-4, wherein the first end of the coupling layer is symmetrical about a central longitudinal axis, and wherein the leg connects to the first end at a position that is located laterally with respect to the central longitudinal axis of the first end.

6. The system of embodiment 5, wherein the longitudinal direction of the leg is oriented substantially parallel to the central longitudinal axis of the first end.

7. The system of embodiment 5 or 6, wherein the leg has a central longitudinal axis, and wherein the central longitudinal axis of the leg is substantially parallel to and spaced a lateral distance from the central longitudinal axis of the first end.

8. The system of any of embodiments 5-7, wherein the central longitudinal axis of the first end is oriented substantially along a bridge of the nose when the coupling layer is coupled to the nose.

9. The system of any of embodiments 1-8, wherein the coupling layer is asymmetrical.

10. The system of any of embodiments 1-9, wherein the coupling layer has a "p" or a "q" configuration.

11. The system of any of embodiments 1-10, wherein the longitudinal direction is oriented substantially along or parallel to a longitudinal direction of a nasogastric tube to be secured by the system.

12. The system of any of embodiments 1-11, wherein the longitudinal direction is oriented substantially along or parallel to a bridge of the nose when the system is coupled to the nose.

13. The system of any of embodiments 1-12, wherein the width of the first end of the coupling layer is oriented substantially laterally with respect to a bridge of the nose when coupled to the nose.

14. The system of any of embodiments 1-13, wherein the coupling layer consists essentially of the first end and the leg.

15. The system of any of embodiments 1-14, wherein the leg of the coupling layer is longer in the longitudinal direction than the first end.

16. The system of any of embodiments 1-15, wherein the first end of the coupling layer extends laterally outwardly with respect to the leg of the coupling layer, such that the leg is located within the width of the first end.

17. The system of any of embodiments 1-16, wherein the leg of the coupling layer is linear.

18. The system of any of embodiments 1-17, wherein the leg of the coupling layer has a uniform width.

19. The system of any of embodiments 1-18, wherein the leg of the coupling layer has a varying width that varies with respect to the longitudinal direction.

20. The system of embodiment 19, wherein the leg is widest where the leg connects to the first end.

21. The system of embodiment 19 or 20, wherein the leg is wider toward the first end.

22. The system of any of embodiments 1-21, wherein the first end of the coupling layer has a footprint area of at least 0.5 A.

23. The system of any of embodiments 1-22, wherein the base layer has at least one of a generally triangular shape, a generally trapezoidal shape, and a lobed shape.

24. The system of any of embodiments 1-23, wherein the base layer has lateral symmetry.

25. The system of any of embodiments 1-24, wherein the first end of the coupling layer has a shape that mimics the shape of the base layer.

26. The system of any of embodiments 1-25, wherein the first end of the coupling layer has at least one of a generally trapezoidal shape, a generally rectangular shape, a generally square shape, a generally circular shape, and an oblong shape.

27. The system of any of embodiments 1-26, wherein the leg of the coupling layer is a first leg, and further comprising a second leg extending outwardly from the first leg at an acute angle with respect to the longitudinal direction of the first leg.

28. The system of embodiment 27, wherein the first leg has a length oriented along its longitudinal direction, and wherein the second leg connects to the first leg at a location along the length of the first leg that is spaced a distance from the first end.

29. The system of embodiment 27, wherein the second leg connects to the first end adjacent the location at which the first leg connects to the first end.

30. The system of any of embodiments 27-29, wherein the second leg is elongated along a longitudinal direction that is oriented at an acute angle with respect to the longitudinal direction of the first leg.

31. The system of any of embodiments 27-30, wherein the first end of the coupling layer is laterally symmetrical about a central longitudinal axis, wherein the first leg connects to the first end at a position that is located laterally with respect to a central longitudinal axis of the first end, wherein the longitudinal direction of the first leg is substantially parallel to and spaced from the central longitudinal axis of the first end, and wherein the second leg is elongated along a longitudinal direction that is oriented at an acute angle with respect to the central longitudinal axis of the first end.

32. The system of any of embodiments 1-31, wherein the base layer has a percent elongation of at least 200%.

33. The system of any of embodiments 1-32, wherein the coupling layer has a percent elongation of no greater than 50%.

34. The system of any of embodiments 1-33, wherein the coupling layer has a percent elongation of no greater than 100%.

35. The system of any of embodiments 1-34, wherein the base layer is formed of a stretch release material.

36. The system of any of embodiments 1-35, wherein the coupling layer includes a first major surface configured to be coupled to the second major surface of the base layer, the first major surface comprising an adhesive, and a second major surface opposite the first major surface, wherein the second major surface of at least a portion of the coupling layer includes a release agent for the adhesive.

37. The system of any of embodiments 1-36, wherein the coupling layer includes a first major surface, wherein the coupling layer further includes an adhesive on the first major surface, and wherein the second major surface of the base layer includes a release agent for the adhesive on the first major surface of the coupling layer.

38. The system of any of embodiments 1-37, wherein the coupling layer includes a first major surface, wherein the coupling layer includes a first mating surface of a mechanical fastener on the first major surface, and wherein the second major surface of the base layer comprises a second mating surface of the mechanical fastener configured to engage the first mating surface on the first major surface of the first end of the coupling layer.

39. A kit comprising:
   the nasogastric tube securement system of any of the preceding embodiments, and
   a release liner,
   wherein the base layer and the coupling layer of the nasogastric tube securement system are provided together on the release liner.

40. The kit of embodiment 39, further comprising:
   a first tape strip provided on the release liner, the first tape strip comprising a securing adhesive and configured to be wrapped about at least a portion of a circumference of the nasogastric tube.

41. The kit of embodiment 40, further comprising:
   a second tape strip provided on the release liner, the second tape strip comprising a skin-contact adhesive and configured to be adhered to another portion of the subject's skin.

42. A method of securing a nasogastric tube, the method comprising:
   providing the nasogastric tube securement system of any of embodiments 1-38;

providing a nasogastric tube that has been inserted into a subject's nostril to a desired depth;

adhering the base layer to the top of a subject's nose via the skin-contact adhesive on the first major surface of the base layer;

coupling the first major surface first end of the coupling layer to the second major surface of the base layer; and securing the leg of the coupling layer to the nasogastric tube.

43. The method of embodiment 42, wherein securing the leg of the coupling layer to the nasogastric tube includes wrapping the leg about at least a portion of a circumference of the nasogastric tube.

44. The method of embodiment 42 or 43, further comprising repositioning at least a portion of the first end of the coupling layer on the base layer.

45. The method of any of embodiments 42-44, further comprising:

marking the nasogastric tube to form a mark; and inserting the nasogastric tube into the subject's nostril up to the mark.

46. The method of any of embodiments 42-45, wherein marking the nasogastric tube includes wrapping a tape strip about at least a portion of a circumference of the nasogastric tube.

47. The method of any of embodiments 42-46, further comprising securing a portion of the nasogastric tube to another portion of the subject's body with a tape strip.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

The following working examples are intended to be illustrative of the present disclosure and not limiting.

EXAMPLES

Materials

Materials utilized in the Examples are shown in Table 1.

TABLE 1

| Materials List | | |
| --- | --- | --- |
| Material | Description | Source |
| A - Foam Tape | 3M ™ Polyethylene Foam Medical Tape 1774W, 510 micron, closed cell, polyethylene foam backing, coated with 60 micron thick pressure sensitive acrylate adhesive. | 3M Company, St. Paul, MN |
| B - PU-NW Tape | 3M ™ CoTran ™ 9699 Melt Blown Polyurethane Tape: 254 micron thick polyurethane/polyethylene backing coated with a gentle medical acrylate adhesive | 3M Company, St. Paul, MN |
| C - PU Film Tape | 3M ™ Polyurethane Tape 9834; 20, micron polyurethane film with 25 micron thick gentle medical acrylate adhesive | 3M Company, St. Paul, MN |
| D - coPET Film Drape | 3M ™ Steri-Drape ™ 2 incise drape: 25 micron thick elastomeric copolyester backing coated with 51 micron thick pressure sensitive acrylate adhesive. | 3M Company, St. Paul, MN |
| E - Si Film | SILPURAN ™ Film 2030; medical grade silicone film, 100 micron thick | Wacker Chemie AG, Munich Germany |
| F- PE Tape | 3M ™ Blenderm ™ Surgical Tape 1525 - Polyethylene backing coated with gentle medical acrylate adhesive | 3M Company, St. Paul, MN |
| G - LDPE Film Drape | 3M ™ Steri-Drape ™ incise drape: 30 micron thick low density polyethylene backing coated with 51 micron thick pressure sensitive acrylate adhesive | 3M Company, St. Paul, MN |
| H - coPET-AM Drape | 3M ™ Ioban ™ 2 Antimicrobial Incise Drape; 25 micron thick elastomeric copolyester backing coated with 51 micron thick iodophor impregnated (antimicrobial) pressure sensitive acrylate adhesive | 3M Company, St. Paul, MN |
| I - PET-NW Tape | 3M ™ Spunlaced Polyester Nonwoven Medical Tape 1776: polyester backing, coated with a medical, pressure sensitive acrylate adhesive | 3M Company, St. Paul, MN |
| J- RA-NW Tape | 3M ™ Rayon Acetate Woven Medical Tape 1538; Rayon acetate woven cloth backing coated with a medical, pressure sensitive acrylate adhesive | 3M Company, St. Paul, MN |
| K- RA-MP NW Tape | 3M ™ MICROPORE 1530 Surgical Tape; microporous rayon nonwoven backing coated with a medical, pressure sensitive acrylate adhesive | 3M Company, St. Paul, MN |

TABLE 1-continued

Materials List

| Material | Description | Source |
|---|---|---|
| L - CAT Tape | 3M ™ Cloth Adhesive Tape 2950; high strength cotton backing coated with a medical, pressure sensitive acrylate adhesive | 3M Company, St. Paul, MN |
| M-NW fiber strip | 3M ™ Steri-Strip Skin Closure 1548; nonwoven backing, fiber reinforced with a medical, pressure sensitive acrylate adhesive | 3M Company, St. Paul, MN |

Test Methods

Tensile Test Method

Percent elongation was measured using a Universal test machine available from Kratos Industrial Equipment Ltda., BR, model K2000MP with a load cell of 20 kgf (196 N), depending on the properties of the backing to be tested, and with the gauge distance and the kart speed set according to the backing characteristics, as set forth in Table 2 below.

TABLE 2

Gauge Distance and Test Speed for Elongation Testing

| Conditions | Distance between gauges | Test speed |
|---|---|---|
| <100% Elongation | 100 mm | 100 mm/min |
| between 100-400% | 50 mm | 200 mm/min |
| >400% | 20 mm | 200 mm/min |

Results

Tensile Strength & Percent Elongation

Various backings or tapes useful for base layers and coupling layers of the present disclosure were tested according to the Tensile Test Method to determine the Tensile Strength (kgf; N) and Percent Elongation at break (%). Examples 1-8 represent relatively elastic backings having a percent elongation of at least 100% that can be used as base layers of the present disclosure. Examples 9-13 represent relatively non-elastic backings having a percent elongation of less than 100% that can be used as coupling layers of the present disclosure. Results are shown in Tables 3 and 4.

TABLE 3

Tensile Strength & Percent Elongation for Base Layer backings

| Example | Base Layer Backing | Tensile Strength at break kgf (N) | Elongation max. (%) |
|---|---|---|---|
| 1 | A - Foam Tape (n = 10) | 2.36 (23.1 N) | 491.14 |
| 2 | B - PU-NW Tape (n = 10) | 2.35 (23.0 N) | 485.54 |
| 3 | C - PU Film Tape (n = 10) | 3.31 (32.5 N) | 586.49 |
| 4 | D - coPET Film Drape (n = 10) | 2.62 (25.7 N) | 717.65 |
| 5 | E - Si Film (n = 6) | 0.98 (9.6 N) | 472.48 |
| 6 | F - PE Tape (n = 10) | 4.21 (41.3 N) | 204.32 |
| 7 | G - LDPE Film Drape (n = 10) | 1.86 (18.2 N) | 229.46 |
| 8 | H - coPET-AM Drape (n = 10) | 3.07 (30.1 N) | 835.55 |

TABLE 4

Tensile Strength & Percent Elongation for Coupling Layer backings

| Example | Coupling Layer Backing | Tensile Strength at break kgf (N) | Elongation max. % |
|---|---|---|---|
| 9 | I - PET-NW Tape (n = 10) | 8.29 (81.3 N) | 41.58 |
| 10 | J - RA-NW Tape (n = 10) | 16.54 (162.2 N) | 21.20 |
| 11 | K - RA-MP NW Tape (n = 10) | 3.58 (35.1 N) | 13.02 |
| 12 | L - CAT Tape (n = 9) | 13.65 (133.9 N) | 5.90 |
| 13 | M - NW fiber strip (n = 10) | 10.33 (101.3 N) | 35.40 |

Various features and aspects of the present disclosure are set forth in the following claims.

What is claimed is:

1. A nasogastric tube securement system, the system comprising:
    a base layer configured to be adhered to a nose, the base layer having a first major surface comprising a skin-contact adhesive and a second major surface opposite the first major surface comprising a release coating; and
    a coupling layer comprising:
        a first end comprising an adhesive, to be repositionably coupled to the second major surface of the base layer, and
        a leg connected to and extending from the first end, the leg being elongated along a longitudinal direction, the leg configured to secure a nasogastric tube;
        wherein the leg connects to the first end at a position that is located toward a lateral side of the first end, relative to a lateral center of the first end; and
        wherein the first end is wider than the leg in a lateral direction that is oriented substantially perpendicularly with respect to the longitudinal direction.

2. The system of claim 1, wherein the base layer has a footprint area of A, and wherein the first end of the coupling layer has a footprint area of at least 0.3 A.

3. The system of claim 1, wherein the first end of the coupling layer is symmetrical about the lateral center.

4. The system of claim 1, wherein the first end of the coupling layer is symmetrical about a central longitudinal axis, and wherein the leg connects to the first end at a position that is located laterally with respect to the central longitudinal axis of the first end.

5. The system of claim 1, wherein the coupling layer has a "p" or a "q" configuration.

6. The system of claim 1, wherein the leg of the coupling layer is longer in the longitudinal direction than the first end.

7. The system of claim 1, wherein the leg of the coupling layer is linear.

8. The system of claim 1, wherein the leg of the coupling layer has a uniform width.

9. The system of claim 1, wherein the leg of the coupling layer has a varying width that varies with respect to the longitudinal direction.

10. The system of claim 1, wherein the leg of the coupling layer is a first leg, and further comprising a second leg extending outwardly from the first leg at an acute angle with respect to the longitudinal direction of the first leg.

11. The system of claim 1, wherein the base layer has a percent elongation of at least 200%, and wherein the coupling layer has a percent elongation of no greater than 50%.

12. The system of claim 1, wherein the base layer is formed of a stretch release material.

13. The system of claim 1, wherein the coupling layer includes
a first major surface configured to be coupled to the second major surface of the base layer, the first major surface of the coupling layer comprising the adhesive, and
a second major surface opposite the first major surface of the coupling layer, wherein the second major surface of at least a portion of the coupling layer includes a release agent for the adhesive.

14. The system of claim 1, wherein the coupling layer includes a first major surface, wherein the coupling layer further includes the adhesive on the first major surface, and wherein the second major surface of the base layer includes a release agent for the adhesive on the first major surface of the coupling layer.

15. The system of claim 1, wherein the coupling layer includes a first major surface, wherein the coupling layer includes a first mating surface of a mechanical fastener on the first major surface, and wherein the second major surface of the base layer comprises a second mating surface of the mechanical fastener configured to engage the first mating surface on the first major surface of the first end of the coupling layer.

16. A kit comprising:
the nasogastric tube securement system of claim 1, and
a release liner,
wherein the base layer and the coupling layer of the nasogastric tube securement system are provided together on the release liner.

17. A method of securing a nasogastric tube, the method comprising:
providing the nasogastric tube securement system of claim 1;
providing a nasogastric tube that has been inserted into a subject's nostril to a desired depth;
adhering the base layer to the top of a subject's nose via the skin-contact adhesive on the first major surface of the base layer;
coupling a first end of the first major surface of the coupling layer to the second major surface of the base layer; and
securing the leg of the coupling layer to the nasogastric tube.

18. The method of claim 17, wherein securing the leg of the coupling layer to the nasogastric tube includes wrapping the leg about at least a portion of a circumference of the nasogastric tube.

19. The method of claim 17, further comprising repositioning at least a portion of the first end of the coupling layer on the base layer.

20. A tube securement system comprising:
a base layer having a first major surface comprising an adhesive and a second major surface opposite the first major surface; and
a coupling layer comprising
a first end repositionably coupled to the second major surface of the base layer, and
a first leg connected to and extending from the first end of the coupling layer and is disconnected from the second major surface of the base layer, wherein the leg comprises a securement mechanism; and
a second leg extending outwardly from the first leg at an acute angle with respect to the longitudinal direction of the first leg.

21. The securement system of claim 20, wherein the securement mechanism comprises an adhesive.

* * * * *